US009247921B2

(12) United States Patent
Provost et al.

(10) Patent No.: US 9,247,921 B2
(45) Date of Patent: Feb. 2, 2016

(54) SYSTEMS AND METHODS OF HIGH FRAME RATE STREAMING FOR TREATMENT MONITORING

(71) Applicant: The Trustees of Columbia University in the City of New York, New York, NY (US)

(72) Inventors: Jean Provost, Paris (FR); Elisa E. Konofagou, New York, NY (US); Gary Yi Hou, Campbell, CA (US); Jiangang Chen, He Bei Province (CN)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/300,106

(22) Filed: Jun. 9, 2014

(65) Prior Publication Data
US 2015/0010222 A1    Jan. 8, 2015

Related U.S. Application Data

(60) Provisional application No. 61/832,503, filed on Jun. 7, 2013, provisional application No. 61/983,733, filed on Apr. 24, 2014.

(51) Int. Cl.
G06K 9/00    (2006.01)
A61B 8/00    (2006.01)
(52) U.S. Cl.
CPC ........................................ A61B 8/00 (2013.01)
(58) Field of Classification Search
CPC .................................. A61B 8/00; G06T 11/005
See application file for complete search history.

(56) References Cited

U.S. PATENT DOCUMENTS

| 3,598,111 | A | 8/1971  | Kahn           |
|-----------|---|---------|----------------|
| 4,463,608 | A | 8/1984  | Takeuchi et al.|
| 4,777,599 | A | 10/1988 | Dorogi et al.  |
| 4,832,941 | A | 5/1989  | Berwing et al. |
| 4,858,613 | A | 8/1989  | Fry et al.     |
| 4,882,679 | A | 11/1989 | Tuy et al.     |
| 5,038,787 | A | 8/1991  | Antich et al.  |

(Continued)

FOREIGN PATENT DOCUMENTS

| EP | 0 221 409 | 5/1987  |
| EP | 0 627 206 | 12/1994 |

(Continued)

OTHER PUBLICATIONS

U.S. Appl. No. 11/697,573, Oct. 17, 2013 Final Office Action.

(Continued)

Primary Examiner — Tom Y Lu
(74) Attorney, Agent, or Firm — Baker Botts L.L.P.

(57) ABSTRACT

Systems and techniques of treatment monitoring include acquiring channel data from each of a plurality of channels of a signal array over a plurality of frames, determining a reconstruction matrix based on a reconstruction operation to be performed on the channel data, applying the reconstruction matrix to the channel data to obtain reconstructed channel data, estimating displacement data representing displacement of an object over the frames from the reconstructed channel data; determining a conversion matrix based on a conversion operation to be performed on the reconstructed channel data, and applying the conversion matrix to the reconstructed channel data to obtain a displacement map.

23 Claims, 12 Drawing Sheets

(56) References Cited

U.S. PATENT DOCUMENTS

| | | | |
|---|---|---|---|
| 5,107,837 A | 4/1992 | Ophir et al. | |
| 5,178,147 A | 1/1993 | Ophir et al. | |
| 5,309,914 A | 5/1994 | Ilnuma | |
| 5,433,708 A | 7/1995 | Nichols et al. | |
| 5,435,310 A | 7/1995 | Sheehan et al. | |
| 5,457,754 A | 10/1995 | Han et al. | |
| 5,601,084 A | 2/1997 | Sheehan et al. | |
| 5,606,971 A | 3/1997 | Sarvazyan | |
| 5,662,113 A | 9/1997 | Liu | |
| 5,722,411 A | 3/1998 | Suzuki et al. | |
| 5,741,522 A | 4/1998 | Violante et al. | |
| 5,752,515 A | 5/1998 | Jolesz et al. | |
| 5,810,731 A | 9/1998 | Sarvazyan et al. | |
| 5,840,028 A | 11/1998 | Chubachi et al. | |
| 5,928,151 A | 7/1999 | Hossack et al. | |
| 6,026,173 A | 2/2000 | Svenson et al. | |
| 6,028,066 A | 2/2000 | Unger | |
| 6,102,864 A | 8/2000 | Hatfield et al. | |
| 6,102,865 A | 8/2000 | Hossack et al. | |
| 6,106,465 A | 8/2000 | Napolitano et al. | |
| 6,123,669 A | 9/2000 | Kanda et al. | |
| 6,152,878 A | 11/2000 | Nachtomy et al. | |
| 6,193,951 B1 | 2/2001 | Ottoboni et al. | |
| 6,200,266 B1 | 3/2001 | Shokrollahi et al. | |
| 6,241,675 B1 | 6/2001 | Smith et al. | |
| 6,246,895 B1 | 6/2001 | Plewes | |
| 6,259,943 B1 | 7/2001 | Cosman et al. | |
| 6,270,459 B1 * | 8/2001 | Konofagou | A61B 5/0053 600/449 |
| 6,309,355 B1 | 10/2001 | Cain et al. | |
| 6,312,382 B1 | 11/2001 | Mucci et al. | |
| 6,352,507 B1 | 3/2002 | Torp et al. | |
| 6,413,216 B1 | 7/2002 | Cain et al. | |
| 6,425,867 B1 | 7/2002 | Vaezy et al. | |
| 6,447,450 B1 | 9/2002 | Oldstad | |
| 6,488,629 B1 | 12/2002 | Saetre et al. | |
| 6,491,636 B2 | 12/2002 | Chenal et al. | |
| 6,508,768 B1 | 1/2003 | Hall et al. | |
| 6,529,770 B1 | 3/2003 | Grimblatov | |
| 6,537,217 B1 | 3/2003 | Bjærum et al. | |
| 6,537,221 B2 | 3/2003 | Criton et al. | |
| 6,671,541 B2 | 12/2003 | Bishop et al. | |
| 6,683,454 B2 | 1/2004 | Rehwald et al. | |
| 6,685,641 B2 | 2/2004 | Liu et al. | |
| 6,689,060 B2 | 2/2004 | Phelps et al. | |
| 6,701,341 B1 | 3/2004 | Wu | |
| 6,770,033 B1 | 8/2004 | Fink et al. | |
| 6,875,176 B2 | 4/2005 | Mourad et al. | |
| 6,936,151 B1 | 8/2005 | Lock et al. | |
| 6,994,673 B2 | 2/2006 | Lysyansky et al. | |
| 7,016,719 B2 | 3/2006 | Rudy et al. | |
| 7,055,378 B2 | 6/2006 | Su et al. | |
| 7,136,518 B2 | 11/2006 | Griffin et al. | |
| 7,257,244 B2 | 8/2007 | Miga | |
| 7,331,926 B2 | 2/2008 | Varghese et al. | |
| 7,344,509 B2 | 3/2008 | Hynynen et al. | |
| 7,421,101 B2 | 9/2008 | Georgescu et al. | |
| 7,429,249 B1 | 9/2008 | Winder et al. | |
| 7,449,306 B2 | 11/2008 | Elson et al. | |
| 7,601,122 B2 | 10/2009 | Zagzebski et al. | |
| 7,753,847 B2 | 7/2010 | Greenleaf et al. | |
| 7,809,426 B2 | 10/2010 | Kim et al. | |
| 7,896,821 B1 | 3/2011 | Magnin et al. | |
| 8,029,444 B2 | 10/2011 | Pedrizzetti et al. | |
| 8,150,128 B2 | 4/2012 | Konofagou et al. | |
| 8,208,709 B2 * | 6/2012 | Ding | G06T 5/002 382/131 |
| 8,428,687 B2 | 4/2013 | Konofagou et al. | |
| 9,063,220 B2 * | 6/2015 | Yoda | G01S 7/52034 |
| 2002/0034757 A1 | 3/2002 | Cubicciotti | |
| 2002/0038086 A1 | 3/2002 | Hynynen et al. | |
| 2002/0039594 A1 | 4/2002 | Unger | |
| 2002/0065461 A1 | 5/2002 | Cosman | |
| 2002/0095081 A1 | 7/2002 | Vilsmeier | |
| 2002/0151792 A1 | 10/2002 | Conston et al. | |
| 2002/0169394 A1 | 11/2002 | Eppstein et al. | |
| 2002/0193784 A1 | 12/2002 | McHale et al. | |
| 2003/0097068 A1 | 5/2003 | Hossack et al. | |
| 2003/0125621 A1 | 7/2003 | Drukker et al. | |
| 2003/0171672 A1 | 9/2003 | Vargbese et al. | |
| 2003/0174890 A1 | 9/2003 | Yamauchi | |
| 2003/0220556 A1 | 11/2003 | Porat et al. | |
| 2004/0006266 A1 | 1/2004 | Ustuner et al. | |
| 2004/0049134 A1 | 3/2004 | Tosaya et al. | |
| 2004/0054357 A1 | 3/2004 | O'Donnell | |
| 2004/0059224 A1 | 3/2004 | Varghese et al. | |
| 2004/0092816 A1 | 5/2004 | Ossmann et al. | |
| 2004/0097805 A1 | 5/2004 | Verard et al. | |
| 2004/0172081 A1 | 9/2004 | Wang | |
| 2004/0210134 A1 | 10/2004 | Hynynen et al. | |
| 2004/0210135 A1 | 10/2004 | Hynynen | |
| 2004/0236219 A1 | 11/2004 | Liu et al. | |
| 2004/0249580 A1 | 12/2004 | Pourcelot et al. | |
| 2004/0258760 A1 | 12/2004 | Wheatley et al. | |
| 2005/0004466 A1 | 1/2005 | Hynenen et al. | |
| 2005/0054930 A1 | 3/2005 | Rickets et al. | |
| 2005/0059876 A1 | 3/2005 | Krishnan | |
| 2005/0080336 A1 | 4/2005 | Byrd et al. | |
| 2005/0080469 A1 | 4/2005 | Larson et al. | |
| 2005/0084538 A1 | 4/2005 | Dayton et al. | |
| 2005/0175541 A1 | 8/2005 | Lanza et al. | |
| 2005/0201942 A1 | 9/2005 | Dugstad et al. | |
| 2005/0203395 A1 | 9/2005 | Sui et al. | |
| 2005/0203399 A1 | 9/2005 | Vaezy et al. | |
| 2005/0259864 A1 | 11/2005 | Dickinson et al. | |
| 2005/0267695 A1 | 12/2005 | German | |
| 2005/0277824 A1 | 12/2005 | Aubry et al. | |
| 2005/0277835 A1 | 12/2005 | Angelsen et al. | |
| 2006/0034904 A1 | 2/2006 | Weimann | |
| 2006/0058651 A1 | 3/2006 | Chiao et al. | |
| 2006/0058671 A1 | 3/2006 | Vitek et al. | |
| 2006/0058673 A1 | 3/2006 | Aase et al. | |
| 2006/0074315 A1 | 4/2006 | Liang et al. | |
| 2006/0078501 A1 | 4/2006 | Goertz et al. | |
| 2006/0173320 A1 | 8/2006 | Radulescu | |
| 2006/0241529 A1 | 10/2006 | Hynynen et al. | |
| 2007/0049824 A1 | 3/2007 | Konofagou et al. | |
| 2007/0055179 A1 | 3/2007 | Deem et al. | |
| 2007/0207194 A1 | 9/2007 | Grayburn et al. | |
| 2007/0219447 A1 | 9/2007 | Kanai et al. | |
| 2007/0232962 A1 | 10/2007 | Zumeris et al, | |
| 2007/0239001 A1 | 10/2007 | Mehi et al. | |
| 2007/0276242 A1 | 11/2007 | Konofagou et al. | |
| 2007/0276245 A1 | 11/2007 | Konofagou et al. | |
| 2008/0194957 A1 | 8/2008 | Hoctor et al. | |
| 2008/0200417 A1 | 8/2008 | Semple et al. | |
| 2008/0243214 A1 | 10/2008 | Koblish | |
| 2008/0260802 A1 | 10/2008 | Sawhney et al. | |
| 2008/0269606 A1 | 10/2008 | Matsumura | |
| 2008/0269668 A1 | 10/2008 | Keenan et al. | |
| 2008/0285819 A1 | 11/2008 | Konofagou et al. | |
| 2008/0319375 A1 | 12/2008 | Hardy | |
| 2009/0005711 A1 | 1/2009 | Konofagou et al. | |
| 2009/0191244 A1 | 7/2009 | Kheir et al. | |
| 2009/0221916 A1 | 9/2009 | Konofagou et al. | |
| 2009/0247911 A1 | 10/2009 | Novak et al. | |
| 2009/0270790 A1 | 10/2009 | Raghavan | |
| 2010/0286527 A1 | 11/2010 | Cannon et al. | |
| 2011/0098562 A1 | 4/2011 | Salgo et al. | |
| 2011/0208038 A1 | 8/2011 | Konofagou et al. | |
| 2011/0295105 A1 | 12/2011 | Konofagou et al. | |
| 2012/0004693 A1 | 1/2012 | Lo et al. | |
| 2013/0038479 A1 * | 2/2013 | Eldar | H03M 1/121 341/122 |
| 2013/0046229 A1 | 2/2013 | Konofagou et al. | |
| 2013/0066211 A1 | 3/2013 | Konofagou et al. | |
| 2013/0131495 A1 | 5/2013 | Konofagou et al. | |
| 2013/0195313 A1 * | 8/2013 | Gauthier et al. | A61B 8/0833 382/103 |
| 2013/0289398 A1 | 10/2013 | Borden et al. | |

(56) References Cited

U.S. PATENT DOCUMENTS

2013/0304407 A1* 11/2013 George ............... G01R 25/00
702/72
2013/0315491 A1   11/2013 Konofagou et al.
2014/0114216 A1    4/2014 Konofagou et al.

FOREIGN PATENT DOCUMENTS

| WO | WO 99/37938 | 8/1999 |
|---|---|---|
| WO | WO 2007/148279 | 12/2007 |
| WO | WO 2008/015012 | 2/2008 |
| WO | WO 2008/027520 | 3/2008 |
| WO | WO 2008/062342 | 5/2008 |
| WO | WO 2008/131217 | 10/2008 |
| WO | WO 2008/131302 | 10/2008 |
| WO | WO 2008/157422 | 12/2008 |
| WO | WO 2010/044385 | 4/2010 |
| WO | WO 2010/063951 | 6/2010 |
| WO | WO 2011/028690 | 3/2011 |
| WO | WO 2011/035312 | 3/2011 |

OTHER PUBLICATIONS

U.S. Appl. No. 11/697,573, Sep. 4, 2013 Response to Non-Final Office Action.
U.S. Appl. No. 11/697,573, May 10, 2013 Non-Final Office Action.
U.S. Appl. No. 11/697,573, Jan. 18, 2013 Amendment and Request for Continued Examination (RCE).
U.S. Appl. No. 11/697,573, Jul. 18, 2012 Final Office Action.
U.S. Appl. No. 11/697,573, Jun. 27, 2012 Response to Non-Final Office Action.
U.S. Appl. No. 11/697,573, Jan. 26, 2012 Non-Final Office Action.
U.S. Appl. No. 11/697,573, Aug. 18, 2011 Amendment and Request for Continued Examination (RCE).
U.S. Appl. No. 11/697,573, Mar. 18, 2011 Final Office Action.
U.S. Appl. No. 11/697,573, Dec. 22, 2010 Response to Non-Final Office Action.
U.S. Appl. No. 11/697,573, Jun. 23, 2010 Non-Final Office Action.
U.S. Appl. No. 12/077,612, Mar. 21, 2014 Final Office Action.
U.S. Appl. No. 12/077,612, Jan. 30, 2014 Response to Non-Final Office Action.
U.S. Appl. No. 12/077,612, Aug. 30, 2013 Non-Final Office Action.
U.S. Appl. No. 12/077,612, Oct. 26, 2011 Amendment and Request for Continued Examination (RCE).
U.S. Appl. No. 12/077,612, May 26, 2011 Final Office Action.
U.S. Appl. No. 12/077,612, Mar. 23, 2011 Response to Non-Final Office Action.
U.S. Appl. No. 12/077,612, Nov. 16, 2010 Non-Final Office Action.
U.S. Appl. No. 12/096,254, Mar. 21, 2014 Final Office Action.
U.S. Appl. No. 12/096,254, Dec. 23, 2013 Response to Non-Final Office Action.
U.S. Appl. No. 12/096,254, Dec. 17, 2013 Applicant Initiated Interview Summary.
U.S. Appl. No. 12/096,254, Aug. 23, 2013 Non-Final Office Action.
U.S. Appl. No. 12/096,254, Nov. 30, 2012 Amendment and Request for Continued Examination (RCE).
U.S. Appl. No. 12/096,254, May 31, 2012 Final Office Action.
U.S. Appl. No. 12/096,254, Apr. 4, 2012 Response to Non-Final Office Action.
U.S. Appl. No. 12/096,254, Oct. 5, 2011 Non-Final Office Action.
U.S. Appl. No. 13/019,029, Mar. 21, 2013 Issue Fee payment.
U.S. Appl. No. 13/019,029, Dec. 26, 2012 Notice of Allowance.
U.S. Appl. No. 13/045,070, Nov. 7, 2013 Amendment and Request for Continued Examination (RCE).
U.S. Appl. No. 13/045,070, May 9, 2013 Final Office Action.
U.S. Appl. No. 13/045,070, Dec. 21, 2012 Response to Non-Final Office Action.
U.S. Appl. No. 13/045,070, Jun. 22, 2012 Non-Final Office Action.
U.S. Appl. No. 11/697,579, Nov. 28, 2011 Notice of Abandonment.
U.S. Appl. No. 11/697,579, Apr. 29, 2011 Final Office Action.
U.S. Appl. No. 11/697,579, Feb. 7, 2011 Response to Non-Final Office Action.
U.S. Appl. No. 11/697,579, Aug. 6, 2010 Non-Final Office Action.
U.S. Appl. No. 11/697,579, May 17, 2010 Response to Non-Final Office Action.
U.S. Appl. No. 11/697,579, Nov. 17, 2009 Non-Final Office Action.
U.S. Appl. No. 11/697,579, Oct. 15, 2009 Amendment and Request for Continued Examination (RCE).
U.S. Appl. No. 11/697,579, Jul. 15, 2009 Response to Final Office Action.
U.S. Appl. No. 11/697,579, Apr. 15, 2009 Final Office Action.
U.S. Appl. No. 11/697,579, Jan. 16, 2009 Response to Non-Final Office Action.
U.S. Appl. No. 11/697,579, Jul. 18, 2008 Non-Final Office Action.
U.S. Appl. No. 11/899,004, Jan. 3, 2012 Issue Fee payment.
U.S. Appl. No. 11/899,004, Oct. 4, 2012 Amendment after Allowance.
U.S. Appl. No. 11/899,004, Oct. 3, 2012 Notice of Allowance.
U.S. Appl. No. 11/899,004, 9/223/2011 Amendment and Request for Continued Examination (RCE).
U.S. Appl. No. 11/899,004, Jul. 18, 2011 Notice of Allowance.
U.S. Appl. No. 11/899,004, May 10, 2011 Response to Non-Final Office Action.
U.S. Appl. No. 11/899,004, Feb. 8, 2011 Non-Final Office Action.
U.S. Appl. No. 11/433,510, Oct. 4, 2013 Non-Final Office Action.
U.S. Appl. No. 11/433,510, Mar. 30, 2012 Request for Continued Examination (RCE).
U.S. Appl. No. 11/433,510, Mar. 28, 2012 Advisory Action.
U.S. Appl. No. 11/433,510, Dec. 29, 2011 Response to Final Office Action.
U.S. Appl. No. 11/433,510, Sep. 30, 2011 Final Office Action.
U.S. Appl. No. 11/433,510, May 23, 2011 Response to Non-Final Office Action.
U.S. Appl. No. 11/433,510, Jan. 21, 2011 Non-Final Office Action.
U.S. Appl. No. 11/433,510, Oct. 28, 2010 Response to Non-Final Office Action.
U.S. Appl. No. 11/433,510, Apr. 28, 2010 Non-Final Office Action.
U.S. Appl. No. 11/433,510, Apr. 13, 2010 Amendment and Request for Continued Examination (RCE).
U.S. Appl. No. 11/433,510, Nov. 12, 2009 Final Office Action.
U.S. Appl. No. 11/433,510, Aug. 6, 2009 Response to Non-Final Office Action.
U.S. Appl. No. 11/433,510, Mar. 17, 2009 Non-Final Office Action.
U.S. Appl. No. 13/353,148, Apr. 24, 2014 Non-Final Office Action.
U.S. Appl. No. 13/353,148, Oct. 17, 2013 Final Office Action.
U.S. Appl. No. 13/353,148, Sep. 11, 2013 Response to Non-Final Office Action.
U.S. Appl. No. 13/353,148, Jun. 20, 2013 Non-Final Office Action.
U.S. Appl. No. 13/529,239, Jun. 30, 2014 Amendment and Request for Continued Examination (RCE).
U.S. Appl. No. 13/529,239, Dec. 31, 2013 Final Office Action.
U.S. Appl. No. 13/529,239, Dec. 3, 2013 Response to Non-Final Office Action.
U.S. Appl. No. 13/529,239, Jul. 5, 2013 Non-Final Office Action.
U.S. Appl. No. 13/426,400, May 5, 2014 Non-Final Office Action.
Abbott, et al., "Astrocyte-Endothelial Interactions at the Blood-Brain Barrier", *Nat. Rev. Neurosci.*, 7(1):41-53 (2006).
Ammi, et al., "Ultrasonic contrast agent shell rupture detected by inertial cavitation and rebound signals", *IEEE Transactions*, 53(1):126-136 (2006).
Ashikaga, et al., "Transmural Dispersion of Myofiber Mechanics: Implications for Electrical Heterogeneity In Vivo", *Journal of the American College of Cardiology*, 49(8):909-916 (2007).
Aubry, et al., "Experimental Demonstration of Noninvasive Transskull Adaptive Focusing Based on Prior Computed Tomography Scans", *The Journal of the Acoustical Society of America*, 113:84 (2003).
Avolio, et al., "Effects of aging on changing arterial compliance and left ventricular load in a northern Chinese urban community", *Circulation*, 68(1):50-58 (1983).
Azuma, et al., "Bubble Generation by Standing Wave in Water Surrounded by Cranium With Transcranial Ultrasonic Beam", *Japanese Journal of Applied Physics*, 44:4625-4630 (2005).

(56) References Cited

OTHER PUBLICATIONS

Badke, et al., "Effects of Ventricular Pacing on Regional Left Ventricular Performance in the Dog", *Am J Physiol Heart Circ Physiol.*, 238:H858-867 (1980).
Baron, et al., "Simulation of Intracranial Acoustic Fields in Clinical Trials of Sonothrombolysis", *Ultrasound Med. Biol.*, 35(7):1148-1158 (2009).
Baseri, et al., "Multi-Modality Safety Assessment of Blood-Brain Barrier Opening Using Focused Ultrasound and Definity Microbubbles: A Short-Term Study", *Ultrasound Med. Biol.*, 6(9):1445-1459 (2010).
Behrens, et al., "Low-Frequency, Low-Intensity Ultrasound Accelerates Thrombolysis Through the Skull", *Ultrasound in Medicine & Biology*, 25:269-273 (1999).
Bercoff, et al., "Supersonic Shear Imaging: A New Technique for Soft Tissue Elasticity Mapping", *IEEE Transactions on Ultrasonics Ferroelectrics and Frequency Control*, 51:396-409 (2004).
Berger, et al., "Single-Beat Noninvasive Imaging of Cardiac Electrophysiology of Ventricular Pre-Excitation", *Journal of the American College of Cardiology*, 48:2045-2052 (2006).
Bers, "Cardiac Excitation-Contraction Coupling", *Nature*, 415:198-205 (2002).
Bonnefous, et al, "Time Domain Formulation of Pulse-Doppler Ultrasound and Blood Velocity Estimation by Cross Correlation", *Ultrason Imaging*, 8(2):73-85 (1986).
Brekke, et al., "Tissue Doppler Gated (TDOG) Dynamic Three-Dimensional Ultrasound Imaging of the Fetal Heart", *Ultrasound Obstet Gynecol.*, 24(2):192-198 (2004).
Brooks, et al., "Electrical Imaging of the Heart", *IEEE Signal Processing Magazine*, 14:24-42 (1997).
Brundin, et al., "Restorative Therapies in Parkinson's Disease", *Springer Verlag* (2006).
Campbell, et al., "Mechanisms of Transmurally Varying Myocyte Electromechanics in an Integrated Computational Model", *Philos Transact A Math Phys Eng Sci.*, 366:3361-3380 (2008).
Caskey, et al., "Direct Observations of Ultrasound Microbubble Contrast Agent Interaction With the Microvessel Wall", *J Acoust. Soc. Amer.*, 122(2):1191-1200 (2007).
Caskey, et al., "Microbubble Oscillation in Tubes With Diameters of 12, 25, and 195 Microns", *Appl. Phys. Lett.*, 88(3):033902-1-033902-3 (2006).
Cavaglia, et al., "Regional Variation in Brain Capillary Density and Vascular Response to Ischemia", *Brain Res.*, 910(1-2):81-93 (2001).
Chan, "Transgenic Nonhuman Primates for Neurodegenerative Diseases", *Reproductive Biology and Endocrinology*, 2:39 (2004).
Chang, et al., "3-D US Frame Positioning Using Speckle Decorrelation and Image Registration", *Ultrasound in Medicine and Biology*, pp. 801-812 (2003).
Chen, et al., "Optimization of Ultrasound Parameters for Cardiac Gene Delivery of Adenoviral or Plasmid Deoxyribonucleic Acid by Ultrasound-Targeted Microbubble Destruction", *J. Amer. Coll. Cardiol.*, 42(2):301-308 (2003).
Chen, et al., "Estimation of Displacement Vectors and Strain Tensors in Elastography Using Angular Insonifications", *IEEE Transactions on Medical Imaging*, 23(12):1479-1489 (2004).
Chen, et al., "Engineering Acoustics and ASA Committee on Standards: Sound Intensity Measurements", *J. Acoust. Soc. Am.; 164th Meeting: Acoustical Society of America*, 132(3, Pt. 2):1984 (Sep. 2012).
Chen, et al., "Architectural Acoustics and Noise: Advancements and Best Practices in Instrumentation for Architectural Acoustics and Noise", *J. Acoust. Soc. Am.; 164th Meeting: Acoustical Society of America*, 132(3, Pt. 2):1977-2018 (Sep. 2012).
Choi, et al., "Feasibility of Transcranial, Localized Drug-Delivery in the Brain of Alzheimer's-Model Mice Using Focused Ultrasound", *2005 IEEE Ultrasonics Symposium*, pp. 988-991 (Sep. 18-21, 2005).
Choi, et al., "Molecules of Various Pharmacologically-Relevant Sizes Can Cross the Ultrasound-Induced Blood-Brain Barrier Opening In Vivo", *Ultrasound in Medicine & Biology*, 36(1):58-67 (2009).

Choi, et al., "Noninvasive, Transcranial and Localized Opening of the Blood-Brain Barrier Using Focused Ultrasound in Mice", *Ultrasound in Medicine & Biology*, 33(1):95-104 (2007).
Choi, et al., "Spatio-Temporal Analysis of Molecular Delivery Through the Blood-Brain Barrier Using Focused Ultrasound", *Physics in Medicine and Biology*, 52:5509-5530, (2007).
Choi, et al., "Focused Ultrasound-Induced Molecular Delivery Through the Blood-Brain Barrier", *Presented at the IEEE Symp. Ultrason. Ferroelect. Freq. Control*, New York, NY, pp. 1192-1195 (2007).
Choi, et al., "Delivery of pharmacologically-relevant sized molecules through the ultrasound-induced blood-brain barrier opening in vivo", *Neuroscience*, Chicago, IL, USA, Oct. 17-21, 2009.
Choi, et al., "Noninvasive and Transient Blood-Brain Barrier Opening in the Hippocampus of Alzheimer's Double Transgenic Mice Using Pulsed Focused Ultrasound", *Ultrasonic Imaging*, pp. 189-200 (2008).
Choi, et al., "Optimization of Blood-Brain Barrier Opening in Mice using Focused Ultrasound", *2006 IEEE Ultrasounics Symposium* [online], Jun. 2007.
Choi, et al., "Microbubble-size dependence of focused ultrasound-induced blood-brain barrier opening in mice in vivo", *IEEE transactions on Biomedical Engineering*, 57(1):145-154 (2010).
Chomas, et al., "Threshold of Fragmentation for Ultrasonic Contrast Agents", *J. Biomed. Opt.*, 6(2):141-150 (2001).
Clement, et al., "A Hemisphere Array for Non-Invasive Ultrasound Brain Therapy and Surgery", *Phys Med Biol.*, 45:3707-3719 (2000).
Cobbold, R.S.C., "Foundations of biomedical ultrasound", Biomedical engineering series, Oxford University Press, pp. 422-423(2006).
Connor, et al., "A Unified Model for the Speed of Sound in Cranial Bone Based on Genetic Algorithm Optimization", *Physics in Medicine and Biology*, 47:3925-3944 (2002).
Connor, "Simulation Methods and Tissue Property Models for Non-Invasive Transcranial Focused Ultrasound Surgery", Ph.D. Thesis (2005).
Cordeiro, et al., "Transmural Heterogeneity of Calcium Activity and Mechanical Function in the Canine Left Ventricle", *Am J Physiol. Heart Circ. Physiol.*, 286:H1471-1479 (2004).
Coyle, "Spatial Features of the Rat Hippocampal Vascular System", *Exp. Neurol.*, 58(3): 549-561 (1978).
Coyle, "Arterial Patterns of the Rat Rhinencephalon and Related Structures", *Exp. Neurol.*, 49(3): 671-690 (1975).
Coyle, "Vascular Patterns of the Rat Hippocampal Formation", *Exp. Neurol.*, 52(3): 447-458 (1976).
Crum, et al., "Bjerknes Forces on Bubbles in a Stationary Sound Field", *The Journal of the Acoustical Society of America*, 57(6): 1363-1370 (1975).
Cutnell, et al., (1998). Physics, Fourth Edition. New York. Table of Contents.
Daffertshofer, et al., "Transcranial Low-Frequency Ultrasound-Mediated Thrombolysis in Brain Ischemia: Increased Risk of Hemorrhage With Combined Ultrasound and Tissue Plasminogen Activator: Results of a Phase II Clinical Trial", *Stroke*, 36:1441-146 (2005).
Damianou, et al., "Dependence of ultrasonic attenuation and absorption in dog soft tissues on temperature and thermal dose", *J Acoust Soc Am*, 102(1):628-634 (1997).
Datta, et al., "Correlation of Cavitation With Ultrasound Enhancement of Thrombolysis", *Ultrasound in Medicine & Biology*, 32(8): 1257-1267 (2006).
Declerck, et al., "Left ventricular motion reconstruction from planar tagged MR images: a comparison", *Phys Med Biol.*, 45(6): 1611-1632 (2000).
De Craene, et al., "Temporal diffeomorphic free-form deformation: Application to motion and strain estimation from 3D echocardiography", Medical Image Analysis, 16(2):427-450 (2012).
Deffieux, et al., "Transcranial Focused Ultrasound for Blood-Brain Barrier Opening—Numerical Simulations With In Vitro Validation in Human and Monkey Skulls", *Title page and Table of Contents for the AIUM Annual Convention*, San Diego, CA, (2010).
DeLong, "Primate Models of Movement Disorders of Basal Ganglia Origin", *Trends Neurosci.*, 13(7): 281-285 (1990).

(56) References Cited

OTHER PUBLICATIONS

DuBose, et al., "Confusion and Direction in Diagnostic Doppler Sonography", Journal of Diagnostic Medical Sonography, 25(3):173-177 (2009).
Duck, "Physical Properties of Tissue: A Comprehensive Reference Book", *Academic Press*, London, UK, 1990.
Duerinckx, et al., "In vivo acoustic attenuation in liver: correlations with blood tests and histology", *Ultrasound Imaging*, 14(5):405-413 (1988).
Durrer, et al., "Total Excitation of the Isolated Human Heart", *Circulation*, 41:899-912 (1970).
Edwards, et al., "Effects of Ischemia on Left-Ventricular Regional Function in the Conscious Dog", *American Journal of Physiology*, 240, H413-H420 (1981).
Erpelding, et al., "Bubble-Based Acoustic Radiation Force Using Chirp Insonation to Reduce Standing Wave Effects", *Ultrasound in Medicine & Biology*, 33(2):263-269 (2007).
Everbach, et al., "Cavitational Mechanisms in Ultrasound-Accelerated Thrombolysis At 1 Mhz", *Ultrasound in Medicine & Biology*, 26(7): 1153-1160 (2000).
Faris, et al., "Novel Technique for Cardiac Electromechanical Mapping With Magnetic Resonance Imaging Tagging and an Epicardial Electrode Sock", *Ann Biomed Eng.*, 31:430-440 (2003).
Farook, et al., "Preparation of Microbubble Suspensions by Co-Axial Electrohydrodynamic Atomization", *Med. Eng. Phys.*, 29(7): 749-754 (2007).
Fenster, et al., "Three-dimensional ultrasound imaging", *Phys Med Biol*, 46(5):R67-R99 (2001).
Feshitan et al., "Microbubble Size Isolation by Differential Centrifugation", *Journal of Colloid and Interface Science*, 329: 316-324 (2009).
Fiske, et al., "Special Focus Section: Gene Therapy for Parkinson's Disease", *Experimental Neurology*, 209:28-29 (2008).
Fry, et al., "A Focused Ultrasound System for Tissue Volume Ablation in Deep Seated Brain Sites", *IEEE 1986 Ultrasonics Symposium*, pp. 1001-1004 (1986).
Fry, "Transkull Transmission of an Intense Focused Ultrasonic Beam", *Ultrasound in Medicine & Biology*, 3, p. 179 (1977).
Fujii, et al., "A new method for attenuation coefficient measurement in the liver", *Journal of Ultrasound Medicine*, 21(7):783-788 (2002).
Fung, (1993). Biomechanics—Mechanical Properties of Living Tissues. New York. Table of Contents.
Ganan-Calvo, et al., "Perfectly Monodisperse Microbubbling by Capillary Flow Focusing", *Phys. Rev. Lett.*, 87(27) Pt 1: 274501-1-274501-4 (2001).
Gaud et al., "Acoustic Characterization of Single Ultrasound Contrast Agent Microbubbles", *The Journal of the Acoustic Society of America*, 124(6): 4091 (2008).
Ghosh, et al., "Cardiac Memory in Patients With Wolff-Parkinson-White Syndrome: Noninvasive Imaging of Activation and Repolarization Before and After Catheter Ablation", *Circulation*, 118:907-915 (2008).
Giacobini, "Alzheimer Disease, From Molecular Biology to Therapy", *Advances in Experimental Medicine and Biology*, 429:235-245 (1997).
Greenstein, et al., "Mechanisms of Excitation-Contraction Coupling in an Integrative Model of the Cardiac Ventricular Myocyte", *Biophysical Journal*, 90:77-91 (2006).
Greenwald, "Pulse Pressure and Arterial Elasticity", *Qjm—an International Journal of Medicine*, 95(2): 107-112 (2002).
Gupta, et al., "Changes in Passive Mechanical Stiffness of Myocardial Tissue with Aneurysm Formation", *Circulation*, 89:2315-2326 (1994).
Gurev, et al., "Distribution of Electromechanical Delay in the Heart: Insights From a Three-Dimensional Electromechanical Model", *Biophysical Journal*, 99:745-754 (2010).
Gurev, et al., "In Silico Characterization of Ventricular Activation Pattern by Electromechanical Wave Imaging", *Supplement to Heart Rhythm.*, 6:S357 (2009).

Heimdal, et al., "Real-time Strain Rate Imaging of the Left Ventricle by Ultrasound", *J Am Soc EchocardioG.*, 11(11): 1013-1019 (1998).
Henderson, et al., "Series Elasticity of Heart Muscle During Hypoxia", *Cardiovascular Research*, 5:10-14 (1971).
Housden, et al., "Ultrasonic imaging of 3D displacement vectors using a simulated 2D array and beamsteering", *Ultrasonics*, 53(2):615-621 (2013).
Huang, et al. "Watershed Segmentation for Breast Tumor in 2-D Sonography", *Ultrasound in Medicine and Biology*, pp. 625-632 (2004).
Hynynen, et al., "Demonstration of Potential Noninvasive Ultrasound Brain Therapy Through an Intact Skull", *Ultrasound in Medicine & Biology*, 24(2): 275-283 (1998).
Hynynen, et al., "Noninvasive MR Imaging—Guided Focal Opening of the Blood-Brain Barrier in Rabbits", *Radiology*, 220(3): 640-646 (2001).
Hynynen, et al., "Trans-Skull Ultrasound Therapy: The Feasibility of Using Image-Derived Skull Thickness Information to Correct the Phase Distortion", *IEEE Transactions on Ultrasonics, Ferroelectrics and Frequency Control*, 46(3): 752-755, (1999).
Hynynen, et al., "Focal Disruption of the Blood-Brain Barrier Due to 260-Khz Ultrasound Bursts: A Method for Molecular Imaging and Targeted Drug Delivery", *J. Neurosurg.*, 105(3): 445-454 (2006).
International Search Report for PCT/US2007/019149 dated Feb. 29, 2008.
International Preliminary Report on Patentability, dated Jun. 11, 2008 and Written Opinion for PCT/US2006/061809, dated Oct. 4, 2007.
international Preliminary Report on Patentability, dated Nov. 14, 2007 and Written Opinion for PCT/US2006/018454, dated Aug. 9, 2007.
International Preliminary Report on Patentability, dated Apr. 17, 2007 and Written Opinion for PCT/US2005/037669, Jun. 13, 2006.
International Preliminary Report on Patentability, dated Apr. 17, 2007 and Written Opinion for PCT/US2005/037670, dated Nov. 22, 2006.
International Search Report and Written Opinion for PCT/US2010/049681, dated Dec. 7, 2010.
International Search Report and Written Opinion for PCT/US2010/061742, dated Mar. 1, 2011.
International Search Report and Written Opinion for PCT/US2009/056513, dated Oct. 30, 2009.
International Search Report and Written Opinion for PCT/US2009/052563 dated Oct. 8, 2009.
EPO Search Report and Opinion and Office Action for EP06840017.2 dated Dec. 7, 2009 and Mar. 8, 2010.
International Search Report and Written Opinion for PCT/US2009/056565 dated Nov. 2, 2009.
International Search Report and Written Opinion for PCT/US2006/036460, dated Sep. 5, 2007; International Preliminary Report dated Mar. 26, 2008.
Jagannathan, et al., "High-Intensity Focused Ultrasound Surgery of the Brain: Part 1—A Historical Perspective With Modern Applications", *Neurosurgery*, 64(2): 201-211 (2009).
Jasaityte, et al., "Current state of three-dimensional myocardial strain estimation using echocardiography", *J Am Soc Echocardiogr.*, 26(1):15-28 (2013).
Jensen, et al., "Calculation of Pressure Fields From Arbitrarily Shaped, Apodized, and Excited Ultrasound Transducers", *IEEE Transactions on Ultrasonics, Ferroelectrics and Frequency Control*, 39(2): 262-267 (1992).
Kallel, et al., "A Least-Squares Strain Estimator for Elastography", *Ultrasonic Imaging*, 19:195-208 (1997).
Kanai, et al. "Propagation of Spontaneously Actuated Pulsive Vibration in Human Heart Wall and In Vivo Viscoelasticity Estimation", *IEEE Transactions on Ultrasonics, Ferroelectrics, and Frequency Control*, 52(11): 1931-1942 (2005).
Kanai, et al., "Myocardial Rapid Velocity Distribution", *Ultrasound Med Biol.*, 27(4): 481-498 (2001).
Kanai, et al., "Transcutaneous Measurement of Frequency Dispersion in the Regional Pulse Wave Velocity", *2000 IEEE Ultrasonics Symposium*, pp. 1-4 (2000).

(56) References Cited

OTHER PUBLICATIONS

Kanai, et al., "A New Method for Measuring Small Local Vibrations in the Heart Using Ultrasound", *IEEE Transactions on Biomedical Engineering*, 40(12): 1233-1242 (1993).
Kaufman, et al., "Ultrasound Simulation in Bone," *IEEE Transactions on Ultrasonics Ferroelectrics and Frequency Control*, 55(6): 1205-1218 (2008).
Kimber, et al., "A Comparison of Unipolar and Bipolar Electrodes During Cardiac Mapping Studies", *Pacing Clin Electro.*, 19:1196-1204 (1996).
Kinoshita, et al., "Noninvasive Localized Delivery of Herceptin to the Mouse Brain by MRI-Guided Focused Ultrasound-Induced Blood-Brain Barrier Disruption", *Proceedings of the National Academy of Sciences*, 103(31): 11719-11723 (2006).
Kinoshita, et al., "Targeted Delivery of Antibodies Through the Blood-Brain Barrier by MRI-Guided Focused Ultrasound", *Biochemical and Biophysical Research Communications*, 340:1085-1090 (2006).
Klein, et al., "Interdependency of Local Capillary Density, Blood Flow, and Metabolism in Rat Brains", *Amer. J. Physiol.*, 251(6) Pt 2: H1333-H1340 (1986).
Klempner, et al., "Neutrophil Plasma Membranes I. High-Yield Purification of Human Neutrophil Plasma Membrane Vesicles by Nitrogen Cavitation and Differential Centrifugation", *Journal of Cell Biology*, 86:21-28 (1980).
Konofagou, et al., "Noninvasive electromechanical wave imaging and conduction-relevant velocity estimation in vivo", *Ultrasonics*, 50(2):208-215 (2010).
Konofagou, et al., "Mechanism and Safety At the Threshold of the Blood-Brain Barrier Opening In Vivo", *International Society on Therapeutic Ultrasound (ISTU)*, Aix-en-Provence, France, Sep. 21-24, 2009.
Konofagou, et al., "Noninvasive Electromechanical Wave Imaging and Conduction Velocity Estimation In Vivo", *2007 IEEE Ultrasonics Symposium*, pp. 969-972 (2007).
Konofagou, et al., "A New Elastographic Method for Estimation and Imaging of Lateral Strains, Corrected Axial Strains and Poison's Ratios in Tissues", *Ultrasound in Medicine and Biology*, 24(8):1183-1199 (1998).
Konofagou, et al., "Three-Dimensional Motion Estimation in Elastography", *IEEE Proceedings of the Symposium of Ultrasonics, Ferroelectrics and Frequency Control in Sendai, Japan*, pp. 1745-1748 (1998).
Konofagou, et al., "Myocardial Elastography—Feasibility Study In Vivo", *Ultrasound Med & Biol.*, 28(4):475-482 (2002).
Konofagou, et al. "Elastographic Imaging of the Strain Distribution at the Anterior Cruciate Ligament and ACL-Bone Insertions", *Proceedings of the 2005 IEEE 27th Annual International Conference of the Engineering in Medicine and Biology Society*, pp. 972-975 (Shanghai, China Sep. 1-4, 2005).
Korecka, et al., "Cell-Replacement and Gene-Therapy Strategies for Parkinson's and Alzheimers Disease", *Regen. Med.*, 2(4): 425-446 (2007).
Kremkau, et al., "Ultrasonic Attenuation and Propagation Speed in Normal Human Brain", *The Journal of the Acoustical Society of America*, 70:29 (1981).
Kunz, et al., "The Finite Difference Time Domain Method for Electromagnetics," *CRC Press*, Boca Raton, USA (1993).
Kvale, et al., "Size Fractionation of Gas-Filled Microspheres by Flotation", *Separations Technol.*, 6(4): 219-226 (1996).
Lai, et al., "Introduction to Continuum Mechanics" (Pergamon Pr). 3rd Ed. (1993).
Lee, et al., "Improving Stereotactic Surgery Using 3-D Reconstruction", *IEEE Engineering in Medicine and Biology Magazine*, 21:109-116 (2002).
Lee, et al., "Theoretical Quality Assessment of Myocardial Elastography With In Vivo Validation", *IEEE Transactions, Ultrasonics, Ferroelectrics and Frequency Control*, 54:2233-2245 (2007).

Liu, et al., "Hemorrhage Detection During Focused-Ultrasound Induced Blood-Brain-Barrier Opening by Using Susceptibility-Weighted Magnetic Resonance Imaging", *Ultrasound in Med. & Biol.*, 34(4): 598-606 (2008).
Liu, et al., "Magnetic Resonance Imaging Enhanced by Superparamagnetic Iron Oxide Particles: Usefulness for Distinguishing Between Focused Ultrasound-Induced Blood-Brain Barrier Disruption and Brain Hemorrhage", *J. of Magnetic Resonance Imaging*, 29:31-38 (2009).
Lu, et al., "Design and Experiment of 256-Element Ultrasound Phased Array for Noninvasive Focused Ultrasound Surgery", *Ultrasonics*, 44:e325-e330 (2006).
Luo, et al., "A Fast Normalized Cross-Correlation Method for Motion Estimation", *IEEE Transactions, Ultrasonics, Ferroelectrics and Frequency Control*, 57(6): 1347-1357 (2010).
Luo, et al., "High-Frame Rate, Full-View Myocardial Elastography With Automated Contour Tracking in Murine Left Ventricles In Vivo", *IEEE Transactions, Ultrasonics, Ferroelectrics and Frequency Control*, 55(1): 240-248 (2008).
Luo, et al., "Myocardial Elastography at Both High Temporal and Spatial Resolution for the Detection of Infarcts", *Ultrasound Med. Biol.*, 33(8): 1206-1223 (2007).
Luo, et al., "Pulse Wave Imaging of Normal and Aneurysmal Abdominal Aortas In Vivo", *IEEE Trans. Med. Imaging*, 28(4): 477-486 (2009).
Maleke, et al., "In Vivo Feasibility of Real-Time Monitoring of Focused Ultrasound Surgery (FUS) Using Harmonic Motion Imaging (HMI)", *IEEE Trans. Biomed. Eng.*, 57(1): 7-11 (2010).
Maleke, et al., "Single-Element Focused Ultrasound Transducer Method for Harmonic Motion Imaging", *Ultrasonic Imaging*, 28(3): 144-158 (2006).
Marquet, et al., "Non-Invasive Transcranial Ultrasound Therapy Based on a 3D CT Scan: Protocol Validation and In Vitro Results", *Phys. Med. Biol.*, 54:2597-2613 (2009).
Mazziotta, et al., "A Probabilistic Atlas of the Human Brain: Theory and Rationale for Its Development the International Consortium for Brain Mapping (ICBM)", *Neuroimage*, 2:89-101 (1995).
McDannold, et al., "Targeted Disruption of the Blood-Brain Barrier With Focused Ultrasound: Association With Cavitations Activity", *Physics in Medicine and Biology*, 51:793-808 (2006).
McDannold, et al., "Use of Ultrasound Pulses Combined With Definity for Targeted Blood-Brain Barrier Disruption: A Feasibility Study", *Ultrasound in Medicine & Biology*, 33(4): 584-590 (2007).
McDannold, et al., "MRI-Guided Targeted Blood-Brain Barrier Disruption With Focused Ultrasound: Histological Findings in Rabbits", *Ultrasound Med. Biol.*, 31(11): 1527-1537 (2005).
McDannold, et al., "Blood-Brain Barrier Disruption Induced by Focused Ultrasound and Circulating Preformed Microbubbles Appears to be Characterized by the Mechanical Index", *Ultrasound Med Biol.*, 34(5):834-840 (2008).
McLaughlin, et al., "Piezoelectric Sensor Detemiination of Arterial Pulse Wave Velocity", *Physiol Meas.*, 24(3): 693-702 (2003).
McNally, et al., "Computer Vision Elastography: Speckle Adaptive Motion Estimation for Elastography Using Ultrasound Sequences", *IEEE Transactions on Medical Imaging*, 24(6):755-766 (2005).
Melodelima, et al., "Thermal Ablation by High-Intensity-Focused Ultrasound Using a Toroid Transducer Increases the Coagulated Volume. Results of Animal Experiments", *Ultrasound in Medicine & Biology*, 35(3): 425-435 (2009).
Mitri, et al., "Chirp Imaging Vibro-Acoustography for Removing the Ultrasound Standing Wave Artifact", *IEEE Transactions on Medical Imaging*, 24(10): 1249-1255 (2005).
Mychaskiw, et al., "Optison (FS069) Disrupts the Blood-Brain Barrier in Rats", *Anesthesia & Analgesia*, 91:798 (2000).
Nichols, et al., "Vascular Impedance. In McDonald's: Blood Flow in Arteries: Theoretical, Experimental and Clinical Principles", E. Arnold. London, *Oxford University Press*, Table of Contents (1998).
Ophir, et al., "Elastography: A Quantitative Method for Imaging the Elasticity of Biological Tissues", *Ultrasonic Imaging*, 3(2): 111-134 (1991).
Otani, "Use of ultrasound imaging to map propagating action potential waves in the heart", *Computers in Cardiology*, 36:617-620 (2009).

(56) References Cited

OTHER PUBLICATIONS

Palmeri, et al., "Characterizing acoustic attenuation of homogeneous media using focused impulsive acoustic radiation force", *Ultrason Imaging*, 28(2):114-128 (2006).
Papadakis, Emmauel P., "Ultrasonic Instruments & Devices", Academic Press, 8 pages (1999).
Pardridge, "Drug Targeting to the Brain", *Pharmaceutical Research*, 24:1733-1744 (2007).
Pardridge, "The Blood-Brain Barrier: Bottleneck in Brain Drug Development", *NeuroRx*, 2:3-14 (2005).
Patel, et al., "GDNF Delivery for Parkinson's Disease", *ACTA Neurochirurgica-Supplementum*, 97(2): 135-154 (2007).
Perrot, et al., "ECG-Gated, Mechanical and Electromechanical Wave Imaging of Cardiovascular Tissues In Vivo", *Ultrasound in Medicine & Biology*, 33(7):1075-1085 (2007).
Pernot, et al., "Electromechanical Imaging of the Myocardium at Normal and Pathological States", *2005 IEEE Ultrasonics Symposium*, pp. 1091-1094 (2005).
Philippens, "Non-Human Primate Models for Parkinson's Disease", *Drug Discovery Today: Disease Models*, 5:105-111 (2008).
Pichardo, et al., "Multi Frequency Characterization of Speed of Sound for Longitudinal Transmission on Freshly Excised Human Skulls" *9th International Society on Therapeutic Ultrasound*, p. 136 (2009.).
Prinzen, et al., "The Time Sequence of Electrical and Mechanical Activation During Spontaneous Beating and Ectopic Stimulation", *Eur. Heart J.*, 13:535-543 (1992).
Provost, et al., "Electromechanical Wave Imaging of Normal and Ischemic Hearts In Vivo", *IEEE Trans. Med. Imaging*, 29:625-635 (2010).
Provost, et al., "Mapping of cardiac electrical activation with electromechanical wave imaging: An in silico-in vivo reciprocity study", *Heart Rhythm.*, 8(5):752-759 (2011).
Provost, et al., "Imaging the electromechanical activity of the heart in vivo", *PNAS*, 108(21):8565-8570 (2011).
Qin, et al., "Acoustic Response of Compliable Microvessels Containing Ultrasound Contrast Agents", *Phys. Med. Biol.*, 51:5065-5088 (2006).
Qin, et al., "The Natural Frequency of Nonlinear Oscillation of Ultrasound Contrast Agents in Microvessels", *Ultrasound in Med. & Biol.*, 33(7):1140-1148 (2007).
Ramanathan, et al., "Activation and Repolarization of the Normal Human Heart Under Complete Physiological Conditions", *Proceedings of the National Academy of Sciences*, 103:6309-6314 (2006).
Ramanathan, et al., "Noninvasive Electrocardiographic Imaging for Cardiac Electrophysiology and Arrhythmia", *Nat Med.*, 10:422-428 (2004).
Raymond, et al., "Ultrasound Enhanced Delivery of Molecular Imaging and Therapeutic Agents in Alzheimer's Disease Mouse Models", *PLoS One*, 3(5):e2175 (2008).
Rice, et al., "Approximate Model of Cooperative Activation and Crossbridge Cycling in Cardiac Muscle Using Ordinary Differential Equations", *Biophys. J.*, 95:2368-2390 (2008).
Rockenstein, et al., "Transgenic Animal Models of Neurodegenerative Diseases and Their Application to Treatment Development", *Adv. Drug Del. Rev.*, 59(11):1093-1102 (2007).
Rogers, et al., "Age-Associated Changes in Regional Aortic Pulse Wave Velocity", *J Am Coll Cardiol.*, 38(4):1123-1129 (2001).
Roth, "Influence of a Perfusing Bath on the Foot of the Cardiac Action Potential", *Circulation Research*, 86:E19-E22 (2000).
Sabraoui, et al., "Feedback Loop Process to Control Acoustic Cavitation", *Ultrasonics Sonochemistry*, 18(2):589-594 (2011).
Samuel, et al., "An Ex Vivo Study of the Correlation Between Acoustic Emission and Microvascular Damage", *Ultrasound Med. Biol.*, 35(9):1574-1586 (2009).
Sanberg, et al., "Brief Communication: Neural Transplants Disrupt the Blood-Brain Barrier and Allow Peripherally Acting Drugs to Exert a Centrally Mediated Behavioral Effect", *Experimental Neurology*, 102:149-152 (1988).
Sandrin, et al., "Time-Resolved Pulsed Elastography with Ultrafast Ultrasonic Imaging", *Ultrason. Imaging*, 21(4): 259-72 (1999).
Sarvazyan, et al., "Shear Wave Elasticity Imaging: A New Ultrasonic Technology of Medical Diagnostics", *Ultrasound Med Biol.*, 24(9): 1419-1435 (1998).
Sassaroli, et al., "Forced Linear Oscillations of Microbubbles in Blood Capillaries", *J. Acoust. Soc. Am.*, 115(6):3235-3243 (2004).
Sassaroli, et al., "Resonance Frequency of Microbubbles in Small Blood Vessels: a Numerical Study", *Phys. Med. Biol.*, 50:5293-5305 (2005).
Sassaroli, et al., "Cavitation Threshold of Microbubbles in Gel Tunnels by Focused Ultrasound", *Ultrasound in Med. & Biol.*, 33(10):1651-1660 (2007).
Schenk, et al., "Immunization With Amyloid-Beta Attenuates Alzheimer-Disease-Like Pathology in the PDAPP Mouse", *Nature*, 400:173-177 (1999).
Scher, et al., "The Pathway of Ventricular Depolarization in the Dog", *Circ Res.*, 4:461-469 (1956).
Schilling, et al., "Simultaneous Endocardial Mapping in the Human Left Ventricle Using a Noncontact Catheter: Comparison of Contact and Reconstructed Electrograms During Sinus Rhythm", *Circulation*, 98:887-98 (1998).
Sengupta, et al., "Electromechanical Activation Sequence in Normal Heart", *Heart Fail Clin.*, 4:303-314 (2008).
Shehata, et al., "Myocardial Tissue Tagging With Cardiovascular Magnetic Resonance", *Journal of Cardiovascular Magnetic Resonance*, 11:55 (2009).
Sheikov, et al., "Brain Arterioles Show More Active Vesicular Transport of Blood-Borne Tracer Molecules Than Capillaries and Venules After Focused Ultrasound-Evoked Opening of the Blood-Brain Barrier", *Ultrasound Med. Biol.*, 32(9): 1399-1409 (2006).
Sheikov, et al., "Cellular Mechanisms of the Blood-Brain Barrier Opening Induced by Ultrasound in Presence of Microbubbles", *Ultrasound Med Biol.*, 30(7): 979-989 (2004).
Sheikov, et al., "Effect of Focused Ultrasound Applied With an Ultrasound Contrast Agent on the Tight Junctional Integrity of the Brain Microvascular Endothelium", *Ultrasound Med. Biol.*, 34(7): 1093-1104 (2008).
Silva, "Nanotechnology Approaches to Crossing the Blood-Brain Barrier and Drug Delivery to the CNS", *BMC Neruosci.*, 9(Suppl 3): S4 (2008).
Siegel, et al., "Neurotrophic Factors in Alzheimer's and Parkinson's Disease Brain", *Brain Research Reviews*, 33:199-227 (2000).
Sinkus, et al., "High-Resolution Tensor MR Elastography for Breast Tumour Detection", *Phys Med Biol.*, 45(6): 1649-1664 (2000).
Sirsi, et al., "Effect of Microbubble Size on Fundamental Mode High Frequency Ultrasound Imaging in Mice", *Ultrasound in Med. & Bio.*, 36(6): 935-948 (2010).
Spach, et al., "Extracellular Discontinuities in Cardiac Muscle—Evidence for Capillary Effects on the Action Potential Foot", *Circulation Research*, 83:1144-1164 (1998).
Stewart, et al., "Blood-Eye Barriers in the Rat: Correlation of Ultrastructure With Function", *J. Comp. Neurol.*, 340(4): 566-576 (1994).
Stieger, et al., "Enhancement of Vascular Permeability With Low-Frequency Contrast-Enhanced Ultrasound in the Chorioallantoic Membrane Model", *Radiology*, 243(1): 112-121 (2007).
Styner, et al., "Automatic Brain Segmentation in Rhesus Monkeys" *2007 Medical Imaging, Proc. of SPIE*, 6512:65122L-1-65122L-8 (2007).
Sutherland, "Color Doppler Myocardial Imaging—Potential Applications in Acquired and Congenital Heart-Disease", *Acta Paediatr.*, 84:40-48 (1995).
Sykova, et al., "Diffusion in Brain Extracellular Space", *Physiol. Rev.*, 88(4): 1277-1340 (2008).
Talu, et al., "Tailoring the Size Distribution of Ultrasound Contrast Agents: Possible Method for Improving Sensitivity in Molecular Imaging" *Mol. Imag.*, 6(6): 384-392 (2007).
Tang, et al., "Standing-Wave Suppression for Transcranial Ultrasound by Random Modulation", *IEEE transactions on Biomedical Engineering*, 57(1):203-205 (2010).
Tanter, et al., "Ultrafast Compound Imaging for 2-D Motion Vector Estimation: Application to Transient Elastography", *IEEE Trans Ultrason Ferroelectr Freq Control*, 49(10): 1363-74 (2002).

(56) References Cited

OTHER PUBLICATIONS

Tanter, et al., "Focusing and Steering Through Absorbing and Aberrating Layers: Application to Ultrasonic Propagation Through the Skull", *The Journal of the Acoustical Society of America*, 103:2403-2410 (1998).

Tavarozzi, et al., "Magnetocardiography: Current Status and Perspectives Part II: Clinical Applications", *Ital Heart J.*, 3:151-165 (2002).

Techavipoo, et al., "Temperature dependence of ultrasonic propagation speed and attenuation in excised canine liver tissue measured using transmitted and reflected pulses", *The Journal of Acoustical Society of America*, 115(6):2859-2865 (2004).

Treat, et al., "Targeted Delivery of Doxorubicin to the Rat Brain At Therapeutic Levels Using MRI-Guided Focused Ultrasound", *Int. J. Cancer*, 121(4): 901-907 (2007).

Tung, et al., "Identifying the Inertial Cavitation Threshold and Skull Effects in a Vessel Phantom Using Focused Ultrasound and Microbubbles", *Ultrasound in Medicine & Biology*, 36(5): 840-852 (2010).

Tung, et al., "Identifying the Inertial Cavitation Threshold in a Vessel Phantom Using Focused Ultrasound and Microbubbles", *The Journal of the Acoustical Society of America*, 124:2486 (2008).

Tung, et al., "Feasibility of Noninvasive Cavitation-Guided Blood-Brain Barrier Opening Using Focused Ultrasound and Microbubbles in Nonhuman Primates", *Applied Physics Letters*, 98(16):163704 (2001).

Tung, et al., "Noninvasive In Vivo Cavitation Threshold Detection During Blood-Brain Barrier Opening Using Focused Ultrasound and the Contrast Agent and Definity", *Joint 159th Meeting of the Acoustic Society of America*, (Apr. 19, 2010).

Tuszynski, et al., "A Phase 1 Clinical Trial of Nerve Growth Factor Gene Therapy for Alzheimer Disease", *Nature Medicine*, 11:551-555 (2005).

Tuszynski, et al., "Nerve Growth Factor Gene Therapy in Alzheimer Disease" *Alzheimer Disease & Associated Disorders*, 21:179-189 (2007).

Unger, E.C. et al., "Therapeutic Applications of Lipid-Coated Microbubbles", *Advanced Drug Delivery Reviews*, 56(9):1291-1314 (2004).

Vappou, et al., "Quantitative Viscoelastic Parameters Measured by Harmonic Motion Imaging", *Phys. Med. Biol.*, 54:3579-3595 (2009).

Walker, et al., "A Fundamental Limit on the Performance of Correlation Based Phase Correction and Flow Estimation Techniques", *IEEE Transactions, Ultrasonics, Ferroelectrics and Frequency Control*, 41(5): 644-654 (1994).

Walker, et al., "A Fundamental Limit on Delay Estimation Using Partially Correlated Speckle Signals", *IEEE Transactions, Ultrasonics, Ferroelectrics and Frequency Control*, 42(2): 301-308 (1995).

Wang, et al., "A Composite Imaging Technique for High Frame-Rate and Full-View Cardiovascular Ultrasound and Elasticity Imaging", *IEEE Transactions, Ultrasonics, Ferroelectrics and Frequency Control*, 55(10): 2221-2233 (2008).

Wang, et al., "A Composite Imaging Technique for High Frame-Rate and Full-View Cardiovascular Ultrasound and Elasticity Imaging", *IEEE International Ultrasonics Symposium*, New York, NY, Oct. 28-31, 2007.

Wang et al., "Qualitative and Quantitative Analysis of the Molecular Delivery Through the Ultrasound-Enhanced Blood-Brain Barrier Opening in the Murine Brain,"*presented at the IEEE Symp. Ultrason. Ferroelectr. Freq. Control*, Beijing, China, 2008.

Wang, et al., "Increased Aortic Stiffness Assessed by Pulse Wave Velocity in Apolipoprotein E-Defcient Mice", *Am J Physiol Heart Circ Physiol.*, 278(2): H428-34 (2000).

Wenk, "A Primate Model of Alzheimer's Disease", *Behavioural Brain Research*, 57:117-122 (1993).

White, et al., "Longitudinal and Shear Mode Ultrasound Propagation in Human Skull Bone", *Ultrasound in Medicine & Biology*, 32:1085-1096 (2006).

Wyman, et al., "Mapping Propagation of Mechanical Activation in the Paced Heart With MRI Tagging", *Am J Physiol Heart Circ Physiol*, 276:H881-891 (1999).

Xu, et al., "Controllable Gas-Liquid Phase Flow Patterns and Monodisperse Microbubbles in a Microfluidic T-Junction Device", *Appl. Phys. Lett.*, 88(13): 133506-1-133506-3 (2006).

Yin, et al., "A Numerical Study of Transcranial Focused Ultrasound Beam Propagation at Low Frequency", *Physics in Medicine and Biology*, 50:1821-1836 (2005).

Yuh, et. al. "Delivery of Systemic Chemotherapeutic Agent to Tumors by Using Focused Ultrasound: Study in a Murine Model", *Radiology*, 234(2): 431-437 (2005).

Zerhouni, et al., "Human Heart: Tagging with MR Imaging—A Method for Noninvasive Assessment of Myocardial Motion", *Radiology*, 169(1): 59-63 (1988).

Zhang, et al., "Noninvasive Three-Dimensional Electrocardiographic Imaging of Ventricular Activation Sequence", *Am J Physiol Heart Circ Physiol.*, 289:H2724-32 (2005).

Zheng, et al., "Ultrasound-Driven Microbubble Oscillation and Translation Within Small Phantom Vessels", *Ultrasound Med. Biol.*, 33(12): 1978-1987 (2007).

Zheng, et al. "High Resolution Ultrasound Elastomicroscopy Imaging of Soft Tissues: System Development and Feasibility; Ultrasound Elastomicroscopy", *Physics in Medicine and Biology*, 49(17):3925-3938 (2004).

Zlokovic, "The Blood-Brain Barrier in Health and Chronic Neurodegenerative Disorders", *Neuron*, 57(2): 178-201 (2008).

Zwanenburg, et al., "Timing of Cardiac Contraction in Humans Mapped by High-Temporal-Resolution MRI Tagging: Early Onset and Late Peak of Shortening in Lateral Wall", *Am J Physiol Heart Circ Physiol.*, 286:H1872-1880 (2004).

Konofagou et al., "Electromechanical Wave Imaging for Noninvasive Mapping of the 3D Electrical Activation Sequence in Canines and Humans In Vivo", Journal of Biomechanics, 45(5):856-864 (2012).

Ohtani, et al., "Transmural Ultrasound-Based Visualization of Patterns of Action Potential Wave Propagation in Cardiac Tissue", Annals Biomedical Engineering, 38(10):3112-3123 (2010).

Zheng, et al., "Ultrasonic measurement of depth-dependent transient behaviors of articular cartilage under compression", *Journal of Biomechanics*, 38:1830-1837 (2005).

Epstein-Barasg, et al., A microcomposite hydrogel for repeated on-demand ultrasound-triggered drug delivery, *Biomaterials*, 31(19):5208-5217 (2010).

Konofagou, et al., "Ultrasound-Induced Blood-Brain Barrier Opening", *Current Pharmaceutical Biotechnology*, 13(7):1332-1345 (2012).

Chen, et al., "The size of blood-brain barrier opening induced by focused ultrasound is dictated by the acoustic pressure", J. Cereb. Blood Flow Metab., 34:1197-1204 (2014).

Carman, et al., "Adenosine receptor signaling modulates permeability of the blood-brain barrier", *The Journal of Neuroscience*, 31(37):13272-13280 (2011).

Shinna, et al., "Realtime tissue elasticity imaging using the combined autocorrelation method", *J. Med. Ultrasonics*, 29(autumn):119-128 (2002).

Ginat, et al., "High-resolution ultrasound elastography of articular cartilage in vitro", Proceedings of the 28th IEEE EMBS Annual International Conference, New York City, USA, pp. 6644-6647 (Aug. 30-Sep. 3, 2006).

U.S. Appl. No. 12/077,612, Sep. 22, 2014 Amendment and Request for Continued Examination (RCE).

U.S. Appl. No. 12/096,254, Sep. 22, 2014 Amendment and Request for Continued Examination (RCE).

U.S. Appl. No. 13/529,239, Sep. 3, 2014 Non-Final Office Action.

European Search Report for EP Application No. 10838238, dated May 6, 2014.

International Search Report and Written Opinion for PCT/US2011/034704, dated Aug. 18, 2011.

Borden et al., "Ultrasound Radiation Force Modulates Ligand Availability on Target Contrast Agents", Mol. Imaging, 5:139-147 (2006).

"Vial", Retrieved from http://en.wikipedia.org/w/index.php?title=Vial&oldid=603936258 [Downloaded on May 20, 2014].

\* cited by examiner (a)

(b)

(c)

(d)

SYSTEMS AND METHODS OF HIGH FRAME RATE STREAMING FOR TREATMENT MONITORING

CROSS-REFERENCE TO RELATED APPLICATIONS

This application claims the benefit of U.S. Provisional Patent Application Nos. 61/832,503, filed Jun. 7, 2013, and 61/983,733, filed Apr. 24, 2014, each of which is incorporated by reference herein in its entirety.

STATEMENT REGARDING FEDERALLY-SPONSORED RESEARCH

This invention was made with government support from the National Institutes of Health under Grant No.s R01HL114358 and R01EB014496. The government has certain rights in the invention.

BACKGROUND

Certain systems and techniques for treatment monitoring utilize separate acquisition and processing units, for example to perform certain processes, such as displacement estimation, offline in a separare hardware unit. To implement such techniques in a clinical setting, it can be desirable to implement a clinically-oriented, fully-integrated high frame rate platform suitable to analyze and stream real-time feedback of treatment assessment to a user.

High frame-rate imaging can be considered in relation to parallel beamforming, which, alone or in combination with fast analog multiplexing, can reconstruct an entire image following a single acoustic transmission with frame rates up to 1000 frames per second. Parallel processing techniques can be implemented and performed in vivo using a phased array configuration, for example "Explososcan", where data acquisition rates can be quadrupled with simultaneously reconstructing four receiving beams per a wide single transmit beam. Certain Graphical Processing Unit (GPU)-based beamforming approaches can further increase the imaging framerate and resolution. Such GPU-based approaches can also achieve high frame rate imaging, including, for example, Synthetic Aperture (SA) imaging and Short-lag Spatial Coherence Imaging (SLSC).

In certain imaging techniques, including ultrasound elasticity imaging, software beamforming techniques utilizing various transmit sequences can achieve high imaging rates and resolution, such as composite imaging, plane-wave or divergent transmit beam. High frame rate elasticity imaging can provide suitable quantitative imaging of tissue properties, for example with estimation of motion generated by external compression or acoustic radiation force such as Transient Elastography, Shear Wave Imaging (SSI), Elastography, ARFI imaging, and Harmonic Motion Imaging.

Certain imaging techniques, including ultrasound elasticity imaging, can utilize previously beamformed RF signals, which can be obtained from the beam reconstruction of the entire field of view through the entire imaging depth. Harmonic Motion Imaging for Focused Ultrasound (HMIFU) is a treatment monitoring technique for High-Intensity Focused Ultrasound (HIFU). HMIFU utilizes an Amplitude-Modulated HIFU beam to induce a localized focal oscillatory motion, which can be simultaneously estimated and imaged by HMI. In localized elasticity imaging for HMIFU, generally only the focal spot is considered as the region of interest. As such, suitable beamforming strategies for HIFU treatment monitoring can be configured to reconstruct only the focal region, which can reduce computational cost and allows real-time streaming of elasticity maps throughout the entire treatment window.

However, there remains an opportunity for improved treatment monitoring systems and techniques, for example to provide improved frame rate, improved spatial resolution, and real-time feedback over an extended monitoring period.

SUMMARY

Systems and techniques for treatment monitoring are disclosed herein.

In one embodiment of the disclosed subject matter, methods are provided for treatment monitoring using acquired channel data from each of a plurality of channels of a signal array over a plurality of frames. An example method includes, determining a reconstruction matrix based on a reconstruction operation to be performed on the channel data, applying the reconstruction matrix to the channel data to obtain reconstructed channel data, estimating displacement data representing displacement of an object over the frames from the reconstructed channel data, determining a conversion matrix based on a conversion operation to be performed on the reconstructed channel data, applying the conversion matrix to the reconstructed channel data to obtain a displacement map; and outputting the displacement map to a display.

In some embodiments, the signal array can include an imaging array. The signal array can include an HIFU transducer.

In some embodiments, the reconstruction operation can include an RF reconstruction operation. Additionally or alternatively, the reconstruction operation can include a GPU-based reconstruction operation. The method can include applying a low pass filter to the reconstructed channel data.

In some embodiments, the estimating the displacement data can be performed using a cross correlation technique. The method can further include applying a temporal low pass filter to the estimated displacement data. The conversion operation can include a scan conversion operation. Additionally or alternatively, the conversion operation can include a GPU-based conversion operation. At least one of the reconstruction matrix and the conversion matrix can include a sparse matrix.

In some embodiments, the method can include outputting the displacement map to a display in communication with the processor.

In another embodiment of the disclosed subject matter, systems are provided for treatment monitoring using acquired channel data from each of a plurality of channels of a signal array over a plurality of frames. An example system includes one or more memories and one or more processors coupled to the one or more memories. The one or more processors are configured to determine a reconstruction matrix based on a reconstruction operation to be performed on the channel data, apply the reconstruction matrix to the channel data to obtain reconstructed channel data, estimate displacement data representing displacement of an object over the frames from the reconstructed channel data, determine a conversion matrix based on a conversion operation to be performed on the reconstructed channel data, and apply the conversion matrix to the reconstructed channel data to obtain a displacement map.

In some embodiments, the system can include a display in communication with the processor configured to output the displacement map.

BRIEF DESCRIPTION OF THE DRAWINGS

FIG. 4(g) is a B-mode image of a representative sample. FIG. 4(h) illustrates focal oscillatory displacement produced by the system.

Throughout the figures and specification the same reference numerals are used to indicate similar features and/or structures.

DETAILED DESCRIPTION

According to aspects of the disclosed subject matter, systems and methods for treatment monitoring include utilizing a sparse-matrix technique for parallel beamforming and scan conversion to achieve real-time treatment monitoring. It is recognized that the sparse matrix beamforming and reconstruction techniques can be applied to a wide range of imaging and monitoring techniques, including, for example and without limitation, reconstructing data in 3D, trading off the frame rate and motion estimation rates, monitoring treatment in real time and displaying 2D and/or 3D images in real time as well as electronic beam steering and focusing. For purpose of illustration and confirmation of the disclosed subject matter, and without limitation, reference is made to implementing the systems and techniques herein in a fully-integrated, clinically suitable ultrasound scanner with high frame rate real time imaging using HIFU by incorporating a GPU-based algorithm. Such a platform can provide a quantitative real time 2D monitoring feedback during the HIFU treatment directly back to the user.

Harmonic Motion Imaging for Focused Ultrasound (HMIFU) can utilize a single HIFU transducer emitting an amplitude-modulated (AM) beam for inducing both thermal therapy while inducing a stable oscillatory tissue displacement at its focal zone. The oscillatory response, also referred to as HMI displacement, can be estimated using the radio-frequency (RF) signals recorded during the HIFU treatment, as embodied herein, through a confocally-aligned pulse-echo imaging transducer. The localized tissue response can be monitored continuously from the onset of HIFU treatment and can provide the onset of treatment termination to the surgeon based on the change in local tissue stiffness in order to prevent any overtreatment.

Figure 1A:
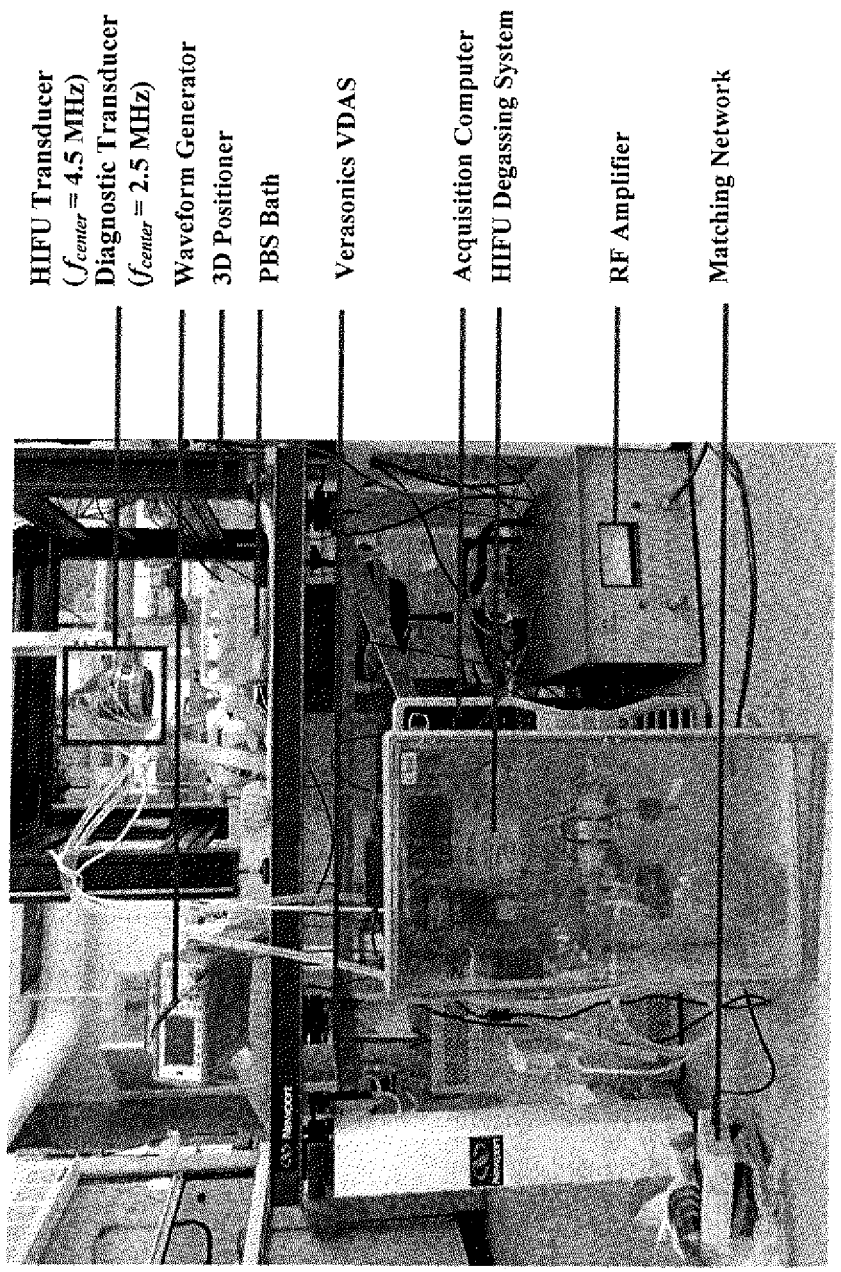
FIG. 1(a) is an image of an exemplary treatment monitoring system according to the disclosed subject matter.
Figure 1B:
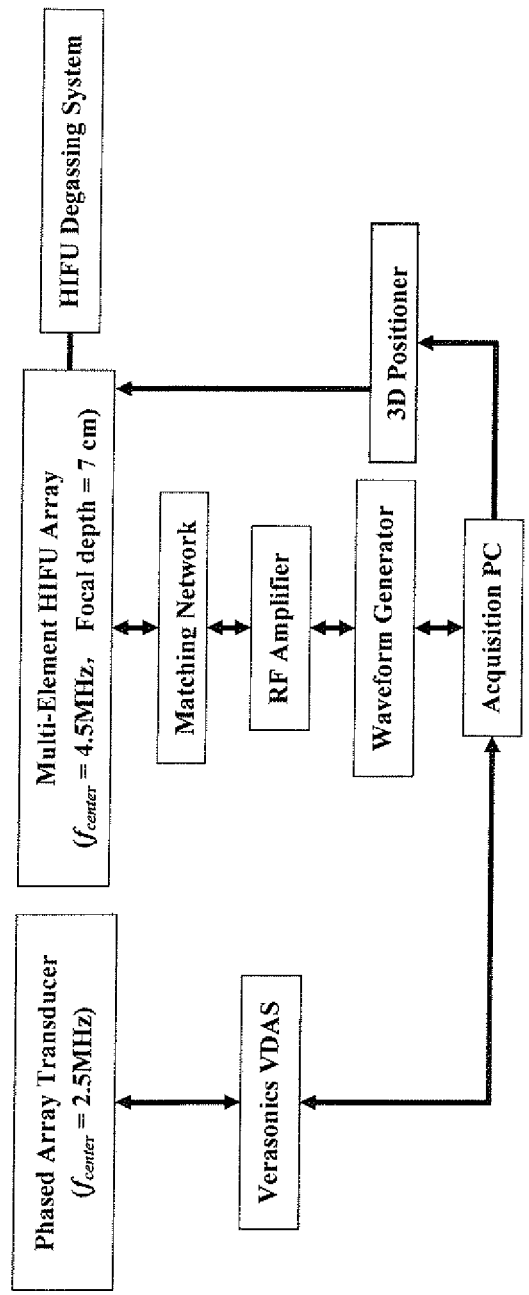
FIG. 1(b) is a diagram illustrating exemplary signal acquisition system for use with the treatment monitoring system of FIG. 1(a).
Figure 1C:
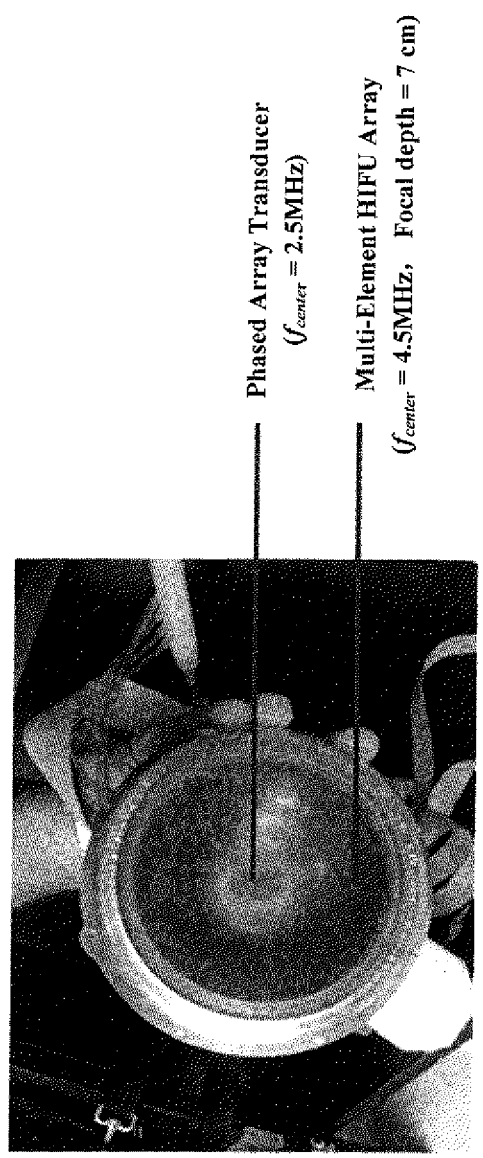
FIG. 1(c) is an image illustrating an exemplary imaging array for use with the treatment monitoring system of FIG. 1(a).

With reference to FIGS. 1(a)-1(c), in an exemplary embodiment of a treatment monitoring system, a 93-element, PZT-4 ceramic HIFU Array (H-178, Sonic Concept Inc., Bothell Wash., U.S.A, $\text{Diameter}_{individual\ element}$=10 mm, $\text{Diameter}_{overall\ outer}$=110 mm, $\text{Diameter}_{overall\ inner}$=41 mm, $f_{center}$=4.5 MHz, Focal depth=70 mm) can be utilized. The geometric and acoustic parameters of the HIFU transducer can be chosen based on the desired application, embodied herein, for purpose of illustration, as a clinical application of localized HIFU treatment on superficial organ applications. The transducer surface can be covered with a polyurethane based membrane, which can be coupled with a sterilization and degassing system (WDS-104, Sonic Concept, Bothell, Wash., U.S.A.) with control of both volume and circulation flow of degassed cooling water within the transducer-tissue interface during HIFU treatment. All channels for the 93 elements can be synchronously excited by an AM-HIFU signal ($f_{carrier}$=4.5 MHz, $f_{AM}$=25 Hz) generated through a dual-channel arbitrary waveform generator (AT33522A, Agilent Technologies Inc., Santa Clara, Calif., U.S.A.). The emitted HIFU beam can be capable of inducing an oscillatory motion at the focal zone in addition to inducing the conventional thermal ablation. The oscillatory motion can be estimated based on the RF signals acquired by a confocally aligned diagnostic transducer in order to achieve real-time HMIFU monitoring during HIFU application.

As embodied herein, the extrapolated in situ focal acoustic pressure and intensity ($I_{sptp}$) can be extrapolated to be 6.5 MPa and 9067 W/cm$^2$, respectively, based on a hydrophone (HGN-0200; Onda Corporation, Sunnyvale, Calif., U.S.A.) calibration procedure. The diagnostic transducer, as embodied herein, can be a 64-element phased array (ATL., Bothell, Wash., U.S.A., $f_{center}$=2.5 MHz) and can be confocally fitted through a circular void or the HIFU transducer aperture through a water-proof mechanical gasket with rotational degree of freedoms. In this manner, the confocally-aligned imaging probe can be adjusted rotationally for adaptive targeting and monitoring at 10 steps with individual step of 36°.

Furthermore, and as embodied herein, the phased array transducer can be operated through a 4-board VDAS system (e.g., Verasonics, Bothell, Wash., U.S.A.) and a 260-pin header connector. The coupled transducer pair can be mounted and stabilized on a 3D translational system (e.g., Velmex Inc., Bloomfield, N.Y., U.S.A.) during both imaging and treatment protocols. The transducer pair can be mechanically translated using the translational system between the imaging or therapy protocols for positioning and alignment adjustment purpose, and can be maintained stationary during the imaging and treatment protocols. With reference to FIGS. 1(a) and 1(b), to synchronize the acquisition of the monitoring signals (i.e., the pulse-echo imaging sequence) with the onset of HIFU treatment, the therapeutic transducer can be triggered with the VDAS imaging system, as embodied herein through a MATLAB-based (Mathworks, Natick, Mass., U.S.A.) algorithm on a host PC (embodied herein as Precision T7500, Dell Inc., Austin, Tex., U.S.A.). Upon the initialization of each imaging or therapy monitoring sequence, the VDAS system can send a trigger signal to the waveform generator, which can activate the emission of the focused ultrasound wave emission from the therapeutic transducer. In this manner, for each imaging or therapy monitoring sequence, the initiation of the emission of focused ultrasound wave (e.g., for inducing both motion and therapy effect) and the emission of diagnostic ultrasound wave (e.g., for detecting the induced motion) can be synchronized through the usage of the VDAS unit controlled through a host PC.

Figure 2:
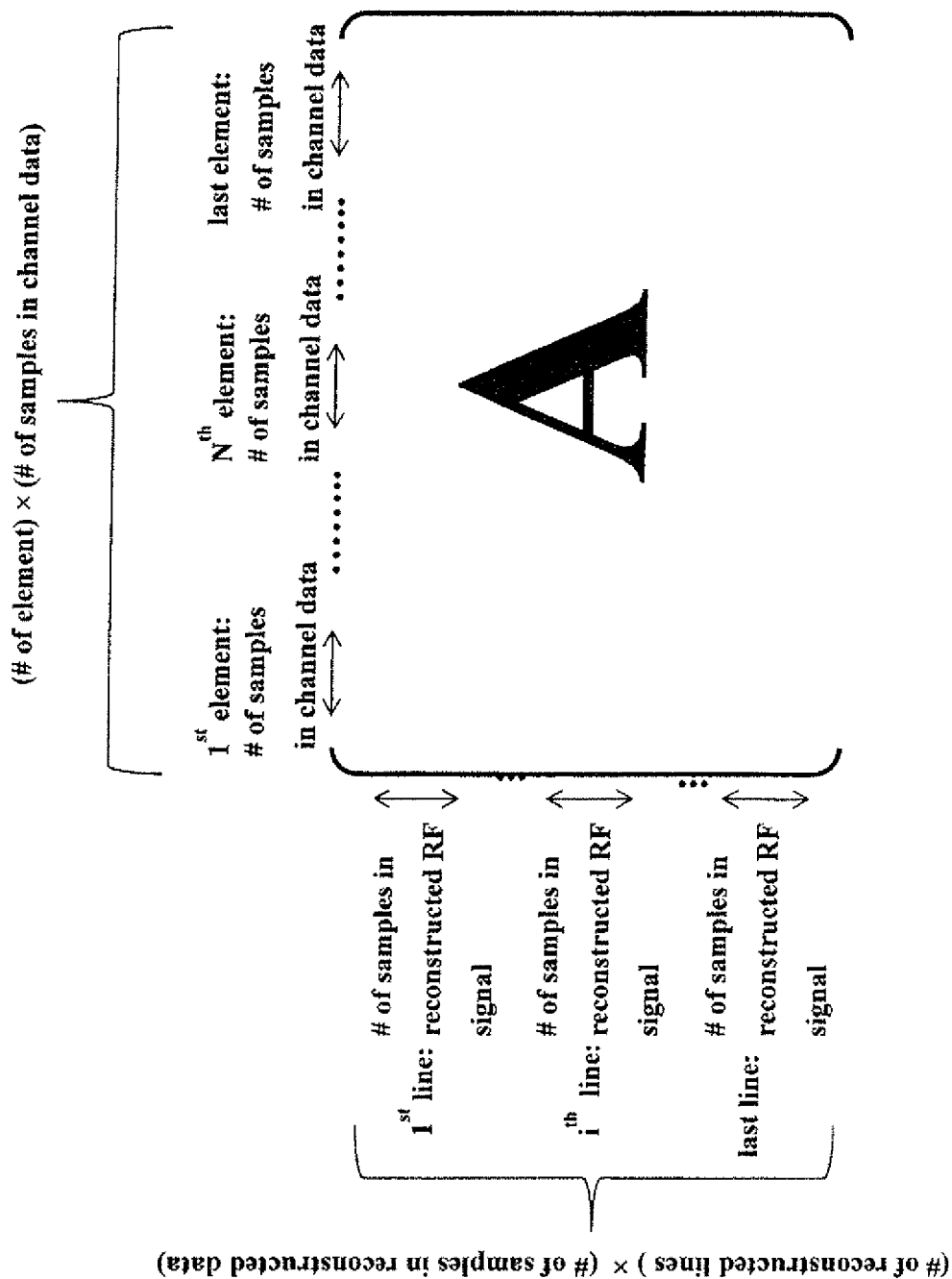
FIG. 2(a) is a diagram illustrating an exemplary reconstruction sparse matrix A.
FIG. 2(b) is a diagram illustrating an exemplary channel data matrix
FIG. 2(c) diagram illustrating an exemplary reconstructed RF data matrix
Figure 2:
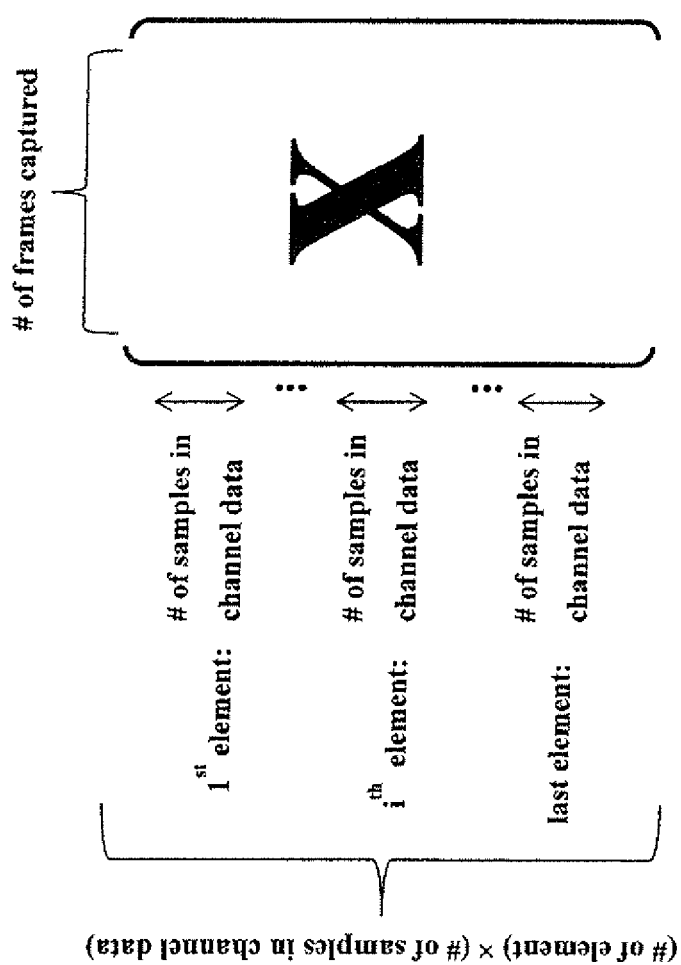
Figure 2:
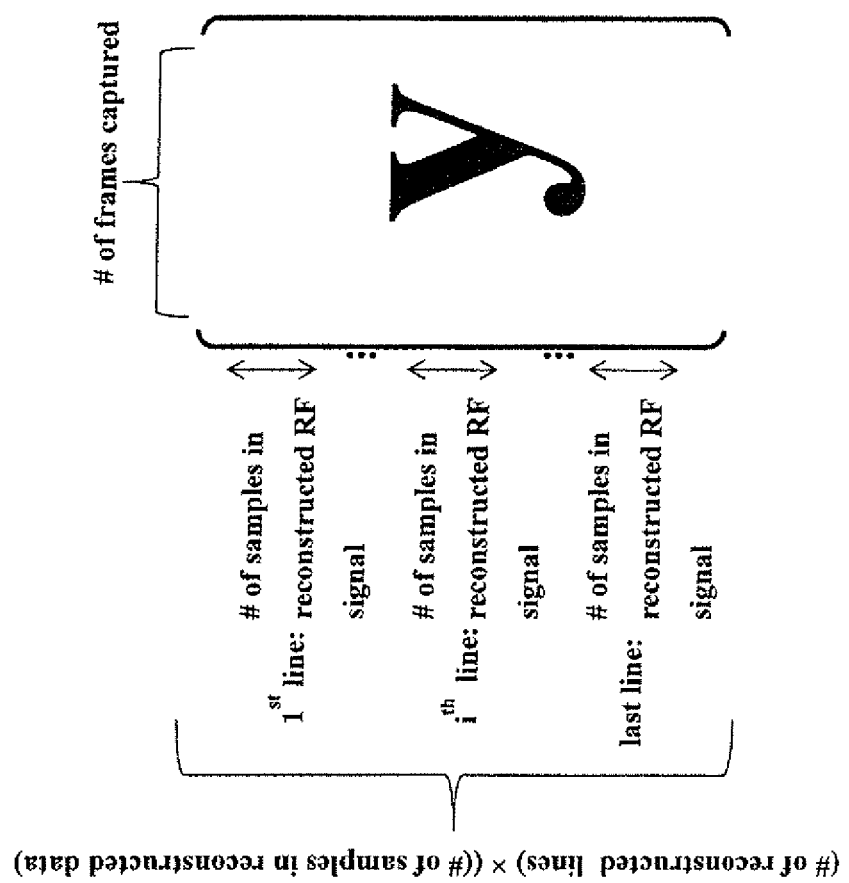

The channel data signals can be individually acquired through a 64-element phased array and the Verasonics system, embodied herein using a single-transmit based divergent wavefront imaging sequence. For example and without limitation, and as embodied herein, the acquisition frame rate can be set at 1000 frames/sec, the analog-to-digital (A/D) sampling can be 10 MHz, which can be suitable for use with a 2.5 MHz diagnostic probe. The acquisition sequence can be repeated continuously, and the acquired frames can be transferred in a stacked set of 10 frames through an external function operated within the host computer, where additional reconstruction algorithms can be applied. Beam-formed radio frequency (RF) frames can also be stored, as described further herein, with reference to FIG. 2(c).

GPU-based algorithms can be utilized to improve processing speeds compared to MATLAB implementations. However, translating MATLAB codes, including codes that can rely on pre-compiled proprietary functions to the Compute Unified Device Architecture (CUDA) language, can be a challenge. The systems and techniques described herein can execute linear operations on the GPU with MATLAB integration. As embodied herein, a sparse matrix option of JACKET package (e.g., from AccelerEyes, Atlanta, Ga. U.S.A.) can be utilized to perform sparse matrix-vector products on the GPU in a MATLAB environment. Linear operations can be represented as a matrix (referred to herein as a "function matrix"). As such, as embodied herein, the function matrix can be utilized to obtain a high performance GPU function of the linear operation using the JACKET package. For purpose of illustration, and not limitation, as embodied herein, interpreted MATLAB algorithms to perform the techniques, which can provide increased flexibility and ease-of-use.

For example, a function $f$ can have input x and output y, which can be a combination of any number of linear operations, including compiled functions such as interp2 in MATLAB. In the following equation, the x and y can be represented as vectors (or matrices) containing a total of N and M elements, respectively. As such, $$y = f(x) \tag{1}$$

Figure 3:
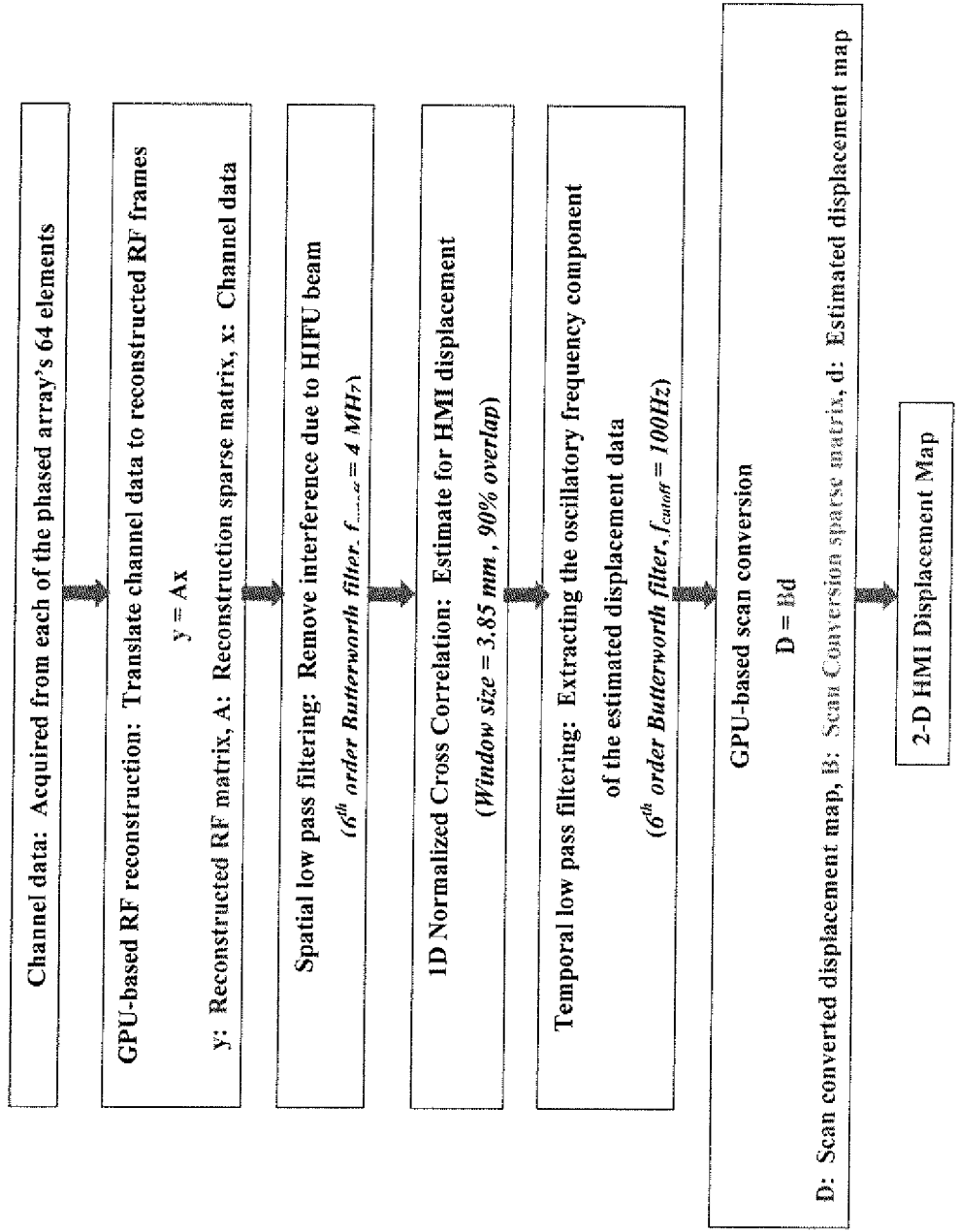
FIG. 3 is a diagram illustrating an exemplary technique for displacement image reconstruction according to the disclosed subject matter.
Figure 4:
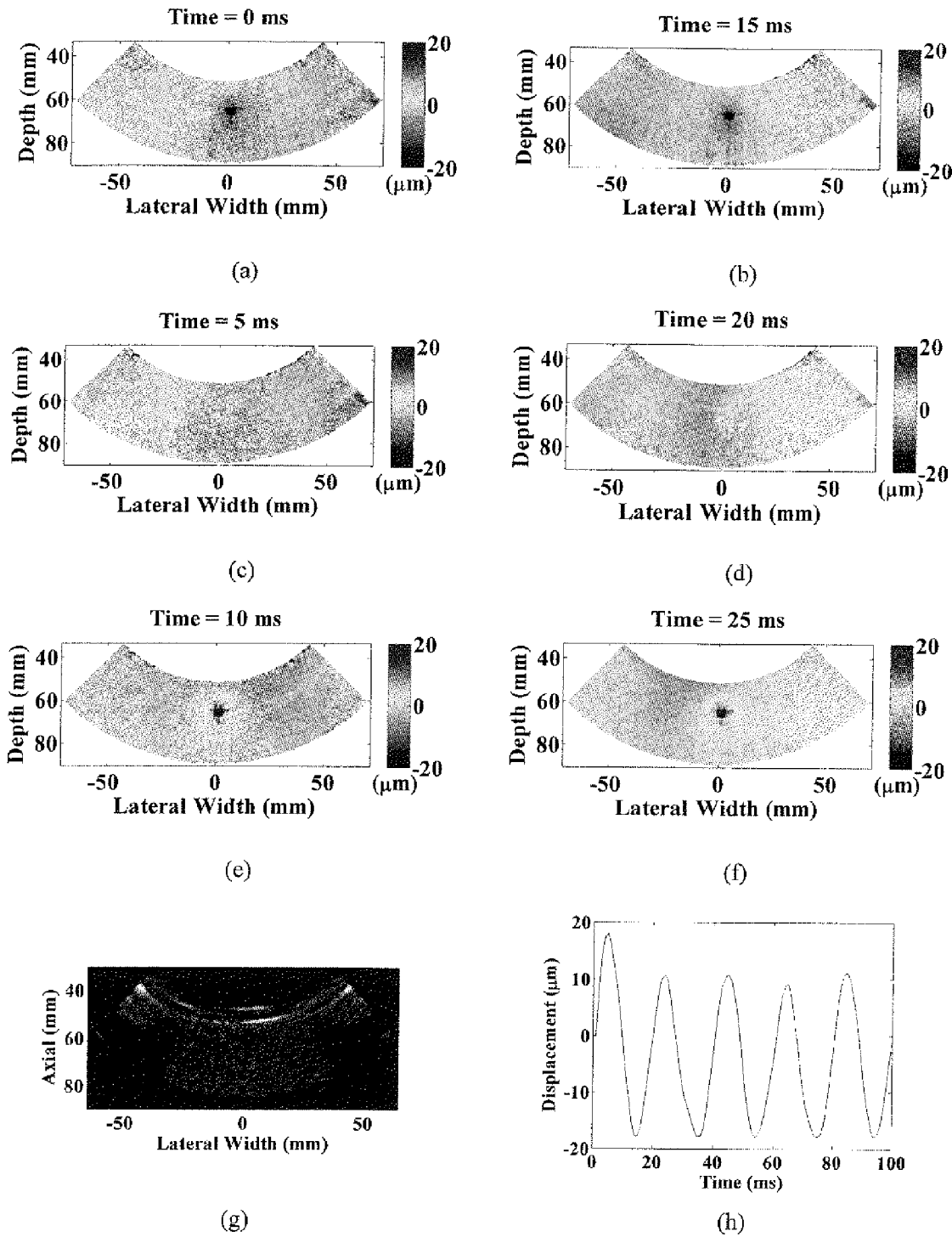
FIGS. 4(a)-4(h) together illustrate exemplary displacement imaging using the treatment monitoring system of FIG. 1a. Three locations, peak negative (a,b), zero (c,d), and peak positive (e,f) displacement during a 50 Hz-cycle across two independent periods are shown, for purpose of illustration.

$f$ can be linear, and thus a matrix A can be determined such that $$y = Ax, \tag{2}$$

where y and x can be represented as vectors in $R^M$ and $R^N$, respectively, without loss of generality. To find A, $f$ can be applied to the $k^{th}$ standard basis vector $e_k$, embodied herein as a vector with zeros everywhere except in the $k^{th}$ position, and can obtain:

$$y = f(e_k), \tag{3}$$

$$y = \sum_j A_{ij} e_k, 1 \le i \le M, \tag{4}$$

$$y = A_{ik}, 1 \le i \le M, \tag{5}$$

or, in other words, f(ek) can represent the kth column of the function matrix. This operation can be repeated for all k to obtain the matrix A. The reconstruction matrix can be used for beamforming a set of any amount of frames, and can host data with varying depth and sampling resolution. An exemplary technique for treatment monitoring, embodied herein using a sparse matrix-based beamforming and reconstruction technique is illustrated in FIG. 3. In some applications, for example when utilizing with images, the function matrix A can be very large. For example and without limitation, as embodied herein, the function matrix A can include from 6×109 to 48×109 elements, and can depend at least in part on the up-sampling rate and spatial size of displacement map reconstruction. As such, sparse matrix formats can be utilized to allocate non-zero elements. For example, to perform 2D linear interpolation, vector x can include N elements corresponding to N pixels of a given image, and y can include M>N elements corresponding to M pixels of the interpolated image. For a 4-neighbor interpolation scheme, an interpolated pixel $y_i$ can be represented as a linear combination of 4 pixels of vector x. The $i^{th}$ line of $A_{ij}$ can thus be used to compute pixel $y_i$, and as embodied herein, can include 4 non-zero values and N-4 zeros, with N typically larger than 10,000. As such, it can be beneficial, both in terms of memory requirements and computational speeds, to represent the matrix A in its sparse form.

Generating the function matrix can be computationally-complex, both in terms of time and memory; however, the function matrix can be computed once, which can expedite the process of generating the function matrix to code compilation. Additionally, in some embodiments, smaller matrices can be obtained from larger matrices by removing appropriate lines of the function matrix, due at least in part to each column of the function matrix corresponding to one pixel of x, and each line of the function matrix corresponding to one pixel in y. As such, the angle field-of-view and the depth in real-time can be adjusted without re-computing the function matrix.

Furthermore, and as embodied herein, linear operations, such as delay-and-sum beamforming and scan conversion, can be represented as matrix-vector products. To obtain each beamformed RF frame, as embodied herein, two sparse matrices can be generated for reconstruction and scan conversion, respectively. For example, each frame of RF data can be reconstructed by multiplying the channel data matrix with the reconstruction sparse matrix, and multiplying the product matrix by another sparse matrix for scan conversion, as illustrated for example in FIG. 3. As embodied herein, each calculation can be performed as a single operation. Furthermore, and as embodied herein, the RF signals can be up-sampled to 80 MHz and reconstructed on a 90 degrees field of view with 128 beam lines, for example for gelatin phantom imaging studies, and can be reduced to 30 degrees with 32 beam lines, for example for purpose of transfer and storage efficiency in HIFU treatment monitoring studies, as described herein. The reconstruction field of view can be chosen larger than the focal excitation zone as the excitation zone can increase with the formation and growth of the thermal lesion. In addition, a larger field of view can provide additional information, such as the propagation of shear waves in the lateral direction. As embodied herein, constructing the sparse matrix function matrix can be performed on the GPU using MATLAB GPU-compatible operations to reduce processing times.

HMIFU systems can incorporate a low-pass filter or band-pass filter to filter out the HIFU frequency in the received echo from diagnostic transducer, and the configuration can depend on the center frequency of the diagnostic probe with respect to the center frequency of the therapeutic probe. For example, and as embodied herein, a 6$^{th}$ order low pass filter with a cutoff frequency at 4 MHz can be applied to the beamformed RF signals to remove the interference HIFU frequency component without affecting the receiving bandwidth of the diagnostic transducer (2-4 MHz).

Additionally, and as embodied herein, a 1-D normalized cross-correlation technique can be used to estimate the axial displacement along each lateral beam lines between two preselected frames within the acquired frames (embodied herein having window size of 3.85 mm and 90% overlap). Another 6$^{th}$ order low pass filter at 100 Hz cutoff frequency can also be applied along the temporal space before construction of the 2D HMI displacement images using the sparse-matrix based scan conversion as described herein, for example with reference to FIG. 3. For purpose of comparison to and confirmation of the disclosed subject matter, another acquisition technique can be utilized to acquire and transfer a separate set of 200 frames and beamformed the frames before being stored in the host computer.

EXAMPLE 1

In one example, for purpose of illustration and confirmation of the disclosed subject matter, a gelatin phantom (n=1, location=3, measurement=3) using gelatin bloom 50 powders (MP Biomedicals LLC., Santa Ana, Calif., U.S.A.) and scatterers using 10% agar powders were provided. As embodied herein, the acoustic attenuation was 0.5 dB/MHz/cm and speed of sound was 1551.7 m/s while the gelatin concentration was 4.9 g/L. The constructed phantom was configured to cure with a cylindrical shape (diameter 120 mm, height 60 mm) with a Young's Modulus of 10 kPa. The phantom was placed on an acoustic absorber to reduce or minimize any interface reflection interference, and degassed echo gel (AQUASONIC®100, Parker Laboratories, Inc., Fairfield, N.J., U.S.A.) was placed above the phantom between the transducer membrane for impedance matching, as shown for example in FIG. 1(a). The imaging sequence included a continuous 1.2 seconds excitation, and data was transferred back to the host PC for a set of 400 ms, equivalent to 20 cycles of HMI excitation. The water in the coupling membrane of the HIFU transducer was degassed for 2 hours prior to treatment monitoring using the circulation system, and acoustic gel was also degassed for one hour prior to treatment monitoring.

Five displacement maps were obtained at three separate locations inside the gelatin phantom. B-mode imaging was performed before each imaging to improve the field of view. For each displacement image, a 1.2 second continuous HMIFU excitation was applied, and the RF signals were recorded at sets of 20-cycles (400 ms). The focal excitation zone was imaged for each location investigated and also centered at the focusing depth of HIFU transducer, embodied herein at 70 mm with −6 dB boundaries encompassing an ellipsoidal shape with diameters of 10 mm (axial) by 5 mm (lateral), as illustrated in FIGS. 4(a)-4(h). The distribution and magnitude range of the displacement profile at maximum excitation (FIG. 4(a), 4(b)), relaxation (FIG. 4(e), 4(f)), and zero (FIG. 4(c), 4(d)) force phase all remained reproducible for each cycle across the entire imaging sequence. Along with the axial displacement from the focal excitation, the estimated displacement within the boundary edge of the phantom includes displacement from the resulted propagation of shear wave associated with each focal excitation. Estimated motion outside the boundary edges of the phantom can be considered to be artifact. The average peak-to-peak HMI displacement at each location was estimated to be 21.9±7.98 µm, 23.9±8.7 µm, and 21.6±2.4 µm, respectively (mean±standard deviation). A full set of displacement frames shown during a 200 ms excitation period allowed vizualization of both focal displacement as well as propagation of shear waves generated from the focal excitation.

EXAMPLE 2

In another example, for purpose of illustration and confirmation of the disclosed subject matter, initial studies (subject=2, lobes=2, treatment location=3) and reproducibility studies (subject=6, lobe=6, treatment location=19) were performed using canine livers excised and immersed into degassed Phosphate buffered saline (PBS) solution bath maintained at temperature of 25° C. The specimens were degassed for two hours prior to treatment monitoring to reduce or prevent any air trapped inside. Each specimen was secured using metallic needles onto an acoustic absorber submerged in a de-ionized and degassed PBS tank, for example as depicted in FIG. 1(a). The HIFU treatment sequence included a continuous 120-seconds excitation, and beamformed RF data frames were transferred back to the host PC at a rate of 100 frames per second, equivalent to 20 cycles of HMI excitation.

Figure 5:
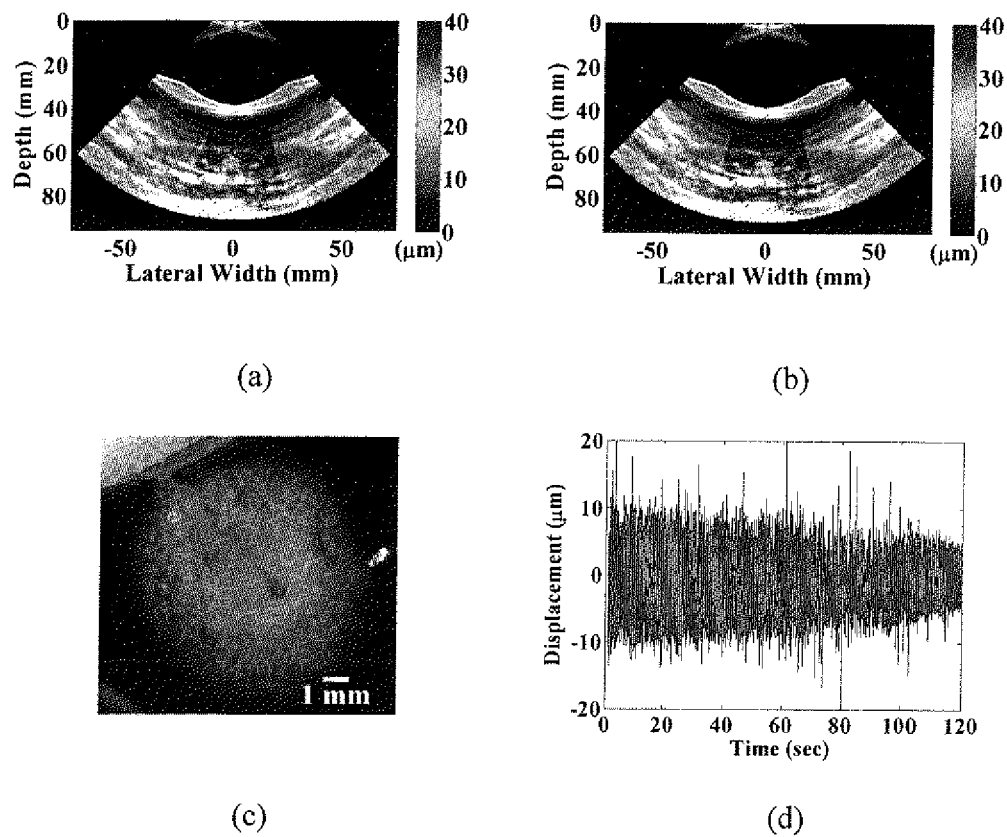
FIGS. 5(a)-5(d) illustrate exemplary B-mode images with peak-to-peak HMI displacement overlay before treatment (a), after treatment (b), the corresponding gross pathology image (c), respectively, along with the focal monitoring displacement across the treatment window (d).
Figure 6:
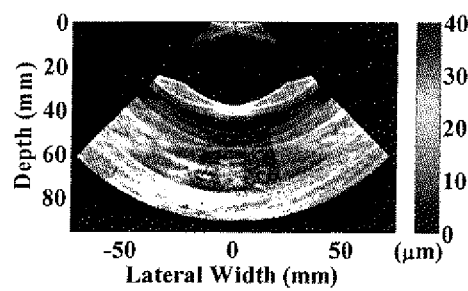
FIGS. 6(a)-6(d) illustrate further exemplary B-mode images with peak-to-peak HMI displacement overlay before treatment (a), after treatment (b), the corresponding gross pathology image (c), respectively, along with the focal monitoring displacement across the treatment window (d).
Figure 6:
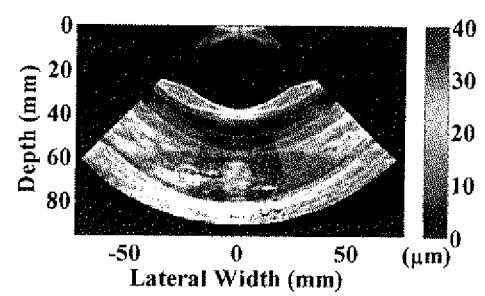
Figure 6:
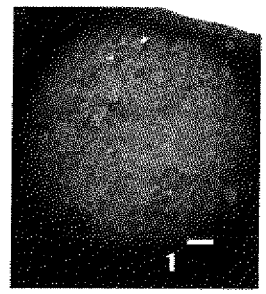
Figure 6:
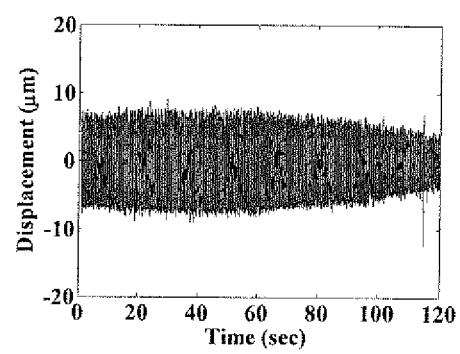
Figure 7:
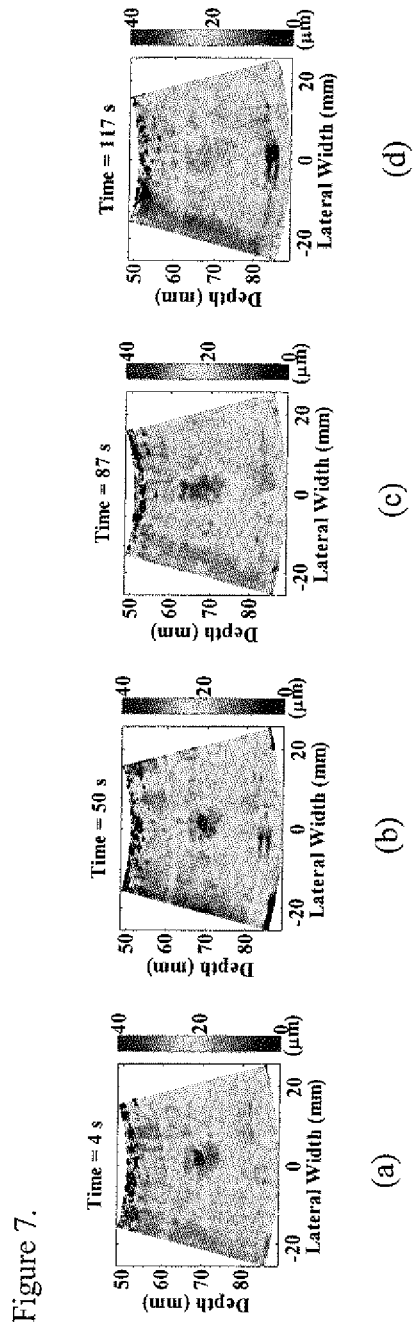
FIG. 7(a)-7(d) illustrate exemplary in vitro peak-to-peak displacement imaging and monitoring of treatment using the system of FIG. 1a. The peak-to-peak displacement frames during a 50 Hz-cycle at representative time points of (a) 4 seconds, (b) 50 seconds, (c) 87 seconds, and (d) 117 seconds are shown.

For each HIFU treatment, conventional B-mode imaging was used to target the focal zone within the region of interest inside the tissue. In the initial study, three HIFU treatments were performed across two liver lobes with HMIFU monitoring. B-mode images were acquired before and after the HIFU treatment, as illustrated in FIGS. 5 and 6, respectively, and used for overlay with peak-to-peak HMI displacement images. The peak-to-peak HMI displacements within the focal excitation region, as illustrated in FIG. 7, were monitored and processed using the technique discussed in Example 1 throughout the entire 2-minutes HIFU treatment period. A full set of displacement frames were shown during a 120-s HIFU treatment period.

Figure 8:
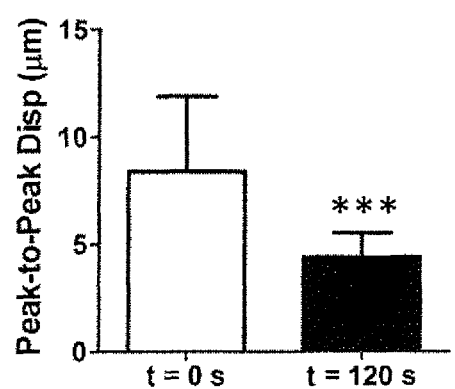
FIG. 8 is a diagram illustrating statistical analysis of exemplary treatment monitoring using the system of FIG. 1(a).

For each of the three initial case studied, a decrease in peak-to-peak HMI displacement of 40%, 30%, and 33% was observed, respectively, as shown in FIGS. 5(f) and 6(f). For the reproducibility cases studied, 18 of the 19 reproducibility study HIFU treatment cases exhibited average displacement decrease of 45.2±20.8%, as illustrated in FIG. 8. The difference between monitoring of displacement at the end of the HIFU treatment was found to be lower than that of the beginning of HIFU treatment (P-value=0.0003). The same decrease trends were also imaged in 2D, where individual single-cycle frame sets including maximum and minimum displacement profiles were shown in FIGS. 5 and 6, representing each of the representative treated locations, respectively. In the initial cases, the detected thermal lesion sizes were also imaged as 251, 254, and 226 mm$^2$ from gross pathology with an expected consistency from the HIFU treatment parameters remaining the same for all cases. In addition, the estimated diameter of HMI focal region from the displacement images across the three treatment cases increased both in axial and lateral direction from before (9.8 mm×8.2 mm, 9.3 mm×7.6 mm, 9.2 mm×6.6 mm, respectively) to after (13.0 mm×11.3 mm, 10.9 mm×8.4 mm, and 10.0 mm×10.5 mm, respectively) HIFU treatment, and thus an estimation of the confirmed thermal lesion diameter from gross pathology (9.0 mm×8.0 mm, 9.0×8.5 mm, 7.5×6.5 mm, respectively) was obtained, as provided in Table 1. The average size of all of the treated thermal lesion sizes in the reproducibility study cases was 236.6±140.2 mm$^2$.

TABLE 1

Comparison table of HMI focal excitation region and the diameter of thermal lesion size from gross pathology analysis following in vitro experiment.

| Treatment Case | Focal excitation diameter at T = 5 s (Axial vs. Lateral) (T = 5 s) | Focal excitation diameter at T = 120 s (Axial vs. Lateral) (T = 120 s) | Thermal lesion diameter from gross pathology (Axial vs. Lateral) |
|---|---|---|---|
| 1 | 9.8 mm × 8.2 mm | 13.0 mm vs. 11.3 mm | 9.0 mm vs. 8.0 mm |
| 2 | 9.3 mm × 7.6 mm | 10.9 mm vs. 8.4 mm | 9.0 mm vs. 8.5 mm |
| 3 | 9.2 mm vs. 6.6 mm | 10.0 mm vs. 10.5 mm | 7.5 mm vs. 6.5 mm |

For purpose of configuration of the disclosed subject matter, in Example 1 and 2, the processing speed of each technique was compared to that of a conventional reconstruction algorithm. In Example 1, the motion display (i.e., processing time from data acquisition to displacement estimation) frame rate was 1 Hz using the GPU-based sparse matrix algorithm, 0.4 Hz using the CPU-based sparse matrix algorithm, and 0.01 Hz using the conventional reconstruction algorithm when reconstructing on a 90° field of view (128 lines) image from 50 to 90 mm deep (9.6 μm axial grid size). In Example 2, the motion display (i.e., processing time from data acquisition to displacement estimation) frame rate was 15 Hz and 5 Hz with reconstructing 32 and 64 RF lines, respectively, using the GPU-based sparse matrix, 2.6 and 1 Hz using the CPU-based sparse matrix algorithm, respectively, and 0.09 and 0.05 Hz using the conventional algorithm for a 40 mm range (9.6 μm axial grid size) and 30 degrees angle field of view image. The results of these comparisons are shown in Table 2.

TABLE 2

Online streaming frame rate using CPU-based conventional reconstruction algorithm, CPU and GPU-based sparse matrix reconstruction algorithm under HMIFU imaging settings for a 40 mm range image with 9.6 μm axial grid size.

| Field of view | Conventional CPU reconstruction | CPU based sparse matrix reconstruction | GPU based sparse matrix reconstruction |
|---|---|---|---|
| 30°, 32 Beams | 0.09 Hz | 2.6 Hz | 15 Hz |
| 30°, 64 Beams | 0.05 Hz | 1 Hz | 5 Hz |
| 90°, 128 Beams | 0.01 Hz | 0.4 Hz | 1 Hz |

The systems and techniques described herein can provide treatment monitoring which can be localized, performed in real time, and does not further delay the treatment procedure. For purpose of illustration and not limitation, referring now to an application of the treatment monitoring systems and techniques disclosed herein to monitoring HIFU treatment, HMIFU is an acoustic radiation force based dynamic elasticity imaging technique using a HIFU transducer for transmitting an AM-HIFU beam to induce a stable focal oscillatory motion, which can be related to the local tissue mechanical property, tracked by 1D cross correlation of RF signal acquired using a confocally-aligned diagnostic transducer. In this application, HMIFU can be utilized to perform localized HIFU monitoring without interrupting the treatment. Real-time HMIFU with capability to stream displacement during the treatment window can thus be performed using a fast beamforming and reconstruction algorithm, as discussed herein. GPU-based beamforming techniques can be utilized for applications of Synthetic Aperture (SA) imaging, real-time small displacement estimation, and Short-lag Spatial Coherence Imaging (SLSC). For purpose of illustration, and as embodied herein, a 2D HMIFU system equipped with a real-time feedback capable of streaming the displacement image during the ablation procedure utilizes a sparse matrix beamforming algorithm implemented on GPU. Additional exemplary applications of HMI are described, for example and without limitation, in International Patent Application No. PCT/US2014/011631, which is incorporated by reference herein in its entirety.

Challenges to real-time treatment monitoring, for example of HIFU treatment, include detecting the onset of lesion formation, providing quantitative mapping of the treated region (i.e., thermal lesion), and performing efficient monitoring without delaying the treatment procedure. Real-time monitoring and quantitatively mapping thermal lesion formation can be performed at a frame rate of 5 to 15 Hz. This approach can facilitates an enhancing temporal resolution to monitor and detect the onset of thermal lesioning indicating effective point of termination. HMIFU can stream the focal displacement map quantitatively delineating the region of thermal lesion based on the stiffness contrast. ARFI and SSI methodologies can implement a cost-effective, all-ultrasound-based HIFU with a monitoring system receiving beamformed RF signals between 11 to 17 kHz. ARFI can utilize a single transducer excited at a low duty cycle (6%) to reduce or prevent transducer damage with the ARFI image displayed interspersed between HIFU treatments at 0.2-Hz frame rate following a single mechanical excitation. SSI also interrupts the treatment for the HIFU beam during the its plane shear wave excitation, allowing a frame rate up to 0.333 Hz. By comparison, HMIFU can continuously streaming focal displacement maps at up to 15 Hz throughout the entire HIFU treatment duration. The HMIFU system utilizes the same HIFU beam for both treatment and elasticity monitoring, and thus can operate in a more efficient monitoring manner by not stopping HIFU treatment to perform the monitoring/imaging sequence. Even in a CPU implementation without the GPU, the sparse matrix based beamforming technique according to the disclosed subject matter can improved the frame rate by 20 to 40 times from that of a conventional delay-and-sum beamforming algorithm between field of view of 30° to 90°.

With reference to Example 1 described herein, the HMI displacement images across the gelatin phantom were reproducible, with the largest variance across locations being under 9.6%. In addition, the focal excitation region was clearly imaged across all cases, where ellipsoidal shaped displaced regions were centered around 70 mm, in agreement with the expected geometrical focal depth of the HIFU transducer. The displacement profile maps measured across different locations showed a strong consistency, thus confirming the reproducibility of beamforming and motion estimation described herein and confirming performance reliability of the disclosed subject matter. While the HMIFU excitation was continuous for 1.2 seconds, tissue heating and the associated changes such as in speed of sound were negligible within the time window and the associated low temperature changes.

For monitoring of HIFU treatment studies, the focal excitation region was also clearly imaged across all the cases, where focal displacement decreased by 40%, 30%, and 33% for each initial feasibility study cases as well as decreased by 45.2±20.8% amongst the reproducibility study cases upon lesion formation with statistical significance (P=0.0003). The displacement decrease began around 60 to 80 seconds upon treatment initiation and progressively continued until the end. The average size of the treated thermal lesions estimated from gross pathology was 236.6±140.2 $mm^2$ under the same treatment parameters, which also confirmed the consistency of the disclosed subject matter.

The examples illustrate real-time, continuous monitoring and lesion imaging of HIFU treatment, which can allow physicians to identify the onset of lesion formation and provide the ability to either terminate the treatment or continue to monitor lesion growth. Steady decrease in the HMI focal displacement, which can indicate the onset of thermal lesion formation due to stiffening of the treated region, was observed throughout HIFU monitoring window in all of the completed treatment cases. In addition, the overlay of a peak-to-peak HMI displacement map onto the B-mode image can depict the quantitative mapping of mechanical property change of the tissue in addition to the anatomical information provided by the B-mode, as illustrated in FIGS. 5 and 6. Compared to the B-mode assessment, shown in FIGS. 5 and 6, of the same regions before and after HIFU ablation, the peak-to-peak HMI displacement images provided improved contrast and mapping of the thermal lesion. The growth of the focal displacement region can be associated with the growing and stiffer thermal lesion. In addition, the displacement images can reproducibly map the changes in mechanical property upon lesion formation.

The single variable sparse matrices described herein can be constructed offline using a separate algorithm prior to treatment monitoring, and the matrix computational cost can vary between few minutes to several hours, and can depend at least in part on the up-sampling rate, beam density, as well as well as field of view. However, the computational cost can be reduced by generating a single matrix at a highest sampling rate and larger fields of view, and adapting the reconstruction matrices with reshaping and down-sampling in respective to the specific imaging parameter. The reconstruction speed can also influence the streaming speed, where a larger field of investigation with higher sampling rate can have a lower streaming frame rate. The data transfer rate from the VDAS to the host computer can also affect speed. For example, as embodied herein, all 200 frames acquired at 1 kHz frame rate were transferred in 930 ms. In some embodiments, frame rates of at least 10-15 Hz can be considered suitable for HIFU guidance.

The systems and techniques according to the disclosed subject matter can be utilized for rapid-prototyping and implementing on any conventional imaging system, including conventional ultrasound systems. The matrix-based algorithms can allow for flexible adaptation of other types of linear functions. The frame rate of 1 kHz, as embodied herein, can be selected to provide suitable displacement quality (i.e., correlation coefficient) and streaming framerate. In addition, at 1 kHz, both monitoring of focal displacement and capturing the propagation of shear waves generated through focal excitation can be performed. The ability to track shear waves can provide additional applications potentials for the disclosed subject matter, including but not limited to simultaneous focal and peripheral-focal region shear-wave based elasticity imaging of lesion formation, as well as assessment of 2D viscoelasticity change during HIFU treatment. Additional applications can include implementation of a raster-ablation sequence for treatment of large tissue volume through electronic beam steering of the 93-element HIFU array, as well as a composite imaging with real time overlaying displacement image onto B-mode to perform simultaneous beam guidance and lesion assessment. Clinical translation of the disclosed subject matter can be applied to breast and pancreatic tumor ablation.

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within its spirit and scope.

The invention claimed is:

1. A method for treatment monitoring using acquired channel data from each of a plurality of channels of a signal array over a plurality of frames, comprising:
   determining, using a processor in communication with the signal array, a reconstruction matrix based on a reconstruction operation to be performed on the channel data;
   applying, using the processor, the reconstruction matrix to the channel data to obtain reconstructed channel data;
   estimating, using the processor, displacement data from the reconstructed channel data, the displacement data representing displacement of an object over the plurality of frames;
   determining, using the processor, a conversion matrix based on a conversion operation to be performed on the reconstructed channel data; and
   applying, using the processor, the conversion matrix to the reconstructed channel data to obtain a displacement map.

2. The method of claim 1, wherein the signal array comprises an imaging array.

3. The method of claim 1, wherein the reconstruction operation comprises an RF reconstruction operation.

4. The method of claim 1, wherein the reconstruction operation comprises a GPU-based reconstruction operation.

5. The method of claim 1, further comprising applying a low pass filter to the reconstructed channel data.

6. The method of claim 1, wherein the estimating the displacement data is performed using a cross correlation technique.

7. The method of claim 1, further comprising applying a temporal low pass filter to the estimated displacement data.

8. The method of claim 1, wherein the conversion operation comprises a scan conversion operation.

9. The method of claim 1, wherein the conversion operation comprises a GPU-based conversion operation.

10. The method of claim 1, wherein at least one of the reconstruction matrix and the conversion matrix is a sparse matrix.

11. The method of claim 1, further comprising outputting the displacement map to a display device in communication with the processor.

12. A system for treatment monitoring using acquired channel data from each of a plurality of channels of a signal array over a plurality of frames, comprising:
    one or more memories; and
    one or more processors coupled to the one or more memories, wherein the one or more processors are configured to:
        determine a reconstruction matrix based on a reconstruction operation to be performed on the channel data;
        apply the reconstruction matrix to the channel data to obtain reconstructed channel data;
        estimate displacement data representing displacement of an object over the frames from the reconstructed channel data;

determine a conversion matrix based on a conversion operation to be performed on the reconstructed channel data; and apply the conversion matrix to the reconstructed channel data to obtain a displacement map.

13. The system of claim 12, wherein the signal array comprises an imaging array.

14. The system of claim 12, wherein the signal array comprises an HIFU transducer.

15. The system of claim 12, wherein the reconstruction operation comprises an RF reconstruction operation.

16. The system of claim 12, wherein the reconstruction operation comprises a GPU-based reconstruction operation.

17. The system of claim 12, wherein the processor is further configured to apply a low pass filter to the reconstructed channel data.

18. The system of claim 12, wherein the displacement data is estimated using a cross correlation technique.

19. The system of claim 12, wherein the processor is further configured to apply a temporal low pass filter to the estimated displacement data.

20. The system of claim 12, wherein the conversion operation comprises a scan conversion operation.

21. The system of claim 12, wherein the conversion operation comprises a GPU-based conversion operation.

22. The system of claim 12, wherein at least one of the reconstruction matrix and the conversion matrix is a sparse matrix.

23. The system of claim 12, further comprising a display, in communication with the processor, to display the displacement map to a user.

* * * * *